United States Patent
Lee et al.

(10) Patent No.: US 12,398,051 B2
(45) Date of Patent: Aug. 26, 2025

(54) FLUID TREATMENT MODULE

(71) Applicant: SEOUL VIOSYS CO., LTD., Gyeonggi-do (KR)

(72) Inventors: Jae Ho Lee, Gyeonggi-do (KR); Jae Young Choi, Gyeonggi-do (KR); Woong Ki Jung, Gyeonggi-do (KR); Kyu Won Han, Gyeonggi-do (KR)

(73) Assignee: SEOUL VIOSYS CO., LTD., Ansan-si (KR)

(*) Notice: Subject to any disclaimer, the term of this patent is extended or adjusted under 35 U.S.C. 154(b) by 1052 days.

(21) Appl. No.: 17/244,425

(22) Filed: Apr. 29, 2021

(65) Prior Publication Data
US 2021/0323840 A1    Oct. 21, 2021

Related U.S. Application Data

(63) Continuation of application No. PCT/KR2019/014173, filed on Oct. 25, 2019.

(30) Foreign Application Priority Data

Oct. 29, 2018 (KR) .......... 10-2018-0129936
Jan. 16, 2019 (KR) .......... 10-2019-0005797

(51) Int. Cl.
C02F 1/32 (2023.01)
F21V 29/503 (2015.01)
F21V 29/70 (2015.01)
F21Y 115/10 (2016.01)

(52) U.S. Cl.
CPC ............ C02F 1/325 (2013.01); F21V 29/503 (2015.01); F21V 29/70 (2015.01); C02F 2201/3222 (2013.01); C02F 2201/3228 (2013.01); C02F 2303/04 (2013.01); F21Y 2115/10 (2016.08)

(58) Field of Classification Search
CPC .... C02F 1/32; C02F 1/325; C02F 2201/3228; C02F 2303/04; C02F 2201/3222; F21V 29/70
See application file for complete search history.

(56) References Cited

U.S. PATENT DOCUMENTS

| | | | | |
|---|---|---|---|---|
| 5,942,110 | A * | 8/1999 | Norris | C02F 1/325 250/431 |
| 7,875,247 | B2 † | 1/2011 | Clark | |
| 9,592,102 | B2 * | 3/2017 | Knight | A61C 17/0202 |
| 2008/0019861 | A1 | 1/2008 | Silderhuis | |
| 2015/0129776 | A1 * | 5/2015 | Boodaghians | C02F 1/325 250/432 R |
| 2015/0144575 | A1 | 5/2015 | Hawkins, II | |
| 2016/0190418 | A1 * | 6/2016 | Inomata | H01L 33/60 257/98 |
| 2018/0140729 | A1 | 5/2018 | Kiuchi et al. | |

FOREIGN PATENT DOCUMENTS

| | | |
|---|---|---|
| CN | 101551094 A | 10/2009 |
| CN | 105209393 A | 12/2015 |
| CN | 107619086 A | 1/2018 |
| JP | 2017051289 | 3/2017 |
| JP | 2017-064610 A | 4/2017 |
| JP | 2018118201 | 8/2018 |
| KR | 1020100104836 | 9/2010 |
| KR | 1020170072054 | 6/2017 |
| WO | 2014187523 A1 † | 11/2014 |
| WO | 2015069680 A1 | 5/2015 |
| WO | 2018048654 A1 | 3/2018 |
| WO | 2018074359 A1 | 4/2018 |

OTHER PUBLICATIONS

International Search Report for International Application PCT/KR2019/014173, mailed Feb. 5, 2020.
Office Action from corresponding European Patent Application No. 19879 809.2, dated Feb. 19, 2024.
English Translation of Office Action from corresponding Chinese Patent Application No. 202010170437.5, dated May 30, 2023 (9 pages).
English translation of Office Action from Korean Patent Application No. 10-2019-0005797, dated Dec. 4, 2023, (24 pages).
Extended / Supplementary European Search Report issued in corresponding EP Application No. 19879809.2, issued Jun. 28, 2022, 9 pages.
Notice from related corresponding European Application No. 19879809.2 , dated Oct. 8, 2024, (8 pages).

* cited by examiner
† cited by third party

*Primary Examiner* — Randy Boyer
(74) *Attorney, Agent, or Firm* — Perkins Coie LLP

(57) ABSTRACT

A fluid treatment module includes a pipe providing a flow channel in which fluid flows, the pipe having an inlet and an outlet, a light source module including a substrate and at least one light emitting diode disposed on an upper surface of the substrate and emitting light into the pipe to treat the fluid, a reflector disposed inside the pipe to reflect the light emitted from the light source module and having higher reflectivity with respect to the light than the pipe, and a heat dissipation plate contacting a rear surface of the substrate to dissipate heat from the light source module. The inlet, the outlet, or both are provided in plural to allow a flow speed and a flow direction of the fluid flowing into the pipe to be controlled, and the heat dissipation plate has higher thermal conductivity than the substrate.

12 Claims, 18 Drawing Sheets

FLUID TREATMENT MODULE

CROSS-REFERENCE OF RELATED APPLICATIONS AND PRIORITY

The Present Application is a continuation application of International Application No. PCT/KR2019/014173 filed Oct. 25, 2019 which claims priority to Korean Application No. 10-2018-0129936 filed Oct. 29, 2018, and Korean Application No. 10-2019-0005797 filed Jan. 16, 2019, the disclosures of which are incorporated by reference in their entirety.

TECHNICAL FIELD

Embodiments of the present invention relate to a fluid treatment module.

BACKGROUND

In recent years, as pollution caused by industrialization is increasing, interest in the environment is increasing together with health consciousness. Accordingly, with increasing demand for clean water or clean air, various related products such as water purifiers and air/water purifiers capable of providing clean water and clean air are being developed.

SUMMARY

Embodiments of the present invention provide a device capable of efficiently treating a fluid, such as air or water.

In accordance with one aspect of the present invention, a fluid treatment module includes: a pipe providing a flow channel in which fluid flows, the pipe having an inlet and an outlet; a light source module including a substrate and at least one light emitting diode disposed on an upper surface of the substrate and emitting light into the pipe to treat the fluid; a reflector disposed inside the pipe to reflect the light emitted from the light source module and having higher reflectivity with respect to the light than the pipe; and a heat dissipation plate contacting a rear surface of the substrate to dissipate heat from the light source module. At least one of the inlet and the outlet is provided in plural to allow a flow speed and a flow direction of the fluid flowing into the pipe to be controlled, and the heat dissipation plate has higher thermal conductivity than the substrate.

In one embodiment, the heat dissipation plate may have a larger area than the substrate.

In one embodiment, the heat dissipation plate may be formed of a metal.

In one embodiment, the inlet and the outlet may be provided in different numbers.

In one embodiment, the pipe may include a body extending in a longitudinal direction thereof and first and second ends disposed in the longitudinal direction of the body.

In one embodiment, the heat dissipation plate may have a larger diameter than the body.

In one embodiment, the inlet and the outlet may be disposed at different end sides.

In one embodiment, the inlet and the outlet may be connected to the pipe in the same direction, with a center of the pipe disposed therebetween, when viewed in the longitudinal direction of the pipe.

In one embodiment, the inlet and the outlet may be connected to the pipe in different directions when viewed in the longitudinal direction of the pipe.

In one embodiment, the fluid treatment module may further include a reflector disposed inside the pipe and reflecting light emitted from the light source module.

In one embodiment, the reflector may have higher reflectivity with respect to the light than the pipe.

In one embodiment, the reflector may include a first reflector disposed on an inner wall of the pipe and a second reflector disposed on the substrate of the light source module. In one embodiment, the second reflector may have an opening exposing the light emitting diode and an inner surface of the opening may be an inclined surface.

In one embodiment, the reflector may be formed of a porous material and may have a reflectivity of 80% or more.

In one embodiment, the inlet may be provided as a pair and the outlet may be provided singularly.

In one embodiment, the inlet and the outlet may have the same diameter or different diameters.

In one embodiment, the fluid treatment module may be employed by a water supply device, which includes a reservoir receiving water and a water treatment device connected to the reservoir and treating the water.

Embodiments of the present invention provide a fluid treatment module having high treatment efficiency and high reliability.

DETAILED DESCRIPTION OF EMBODIMENTS

Figure 1:
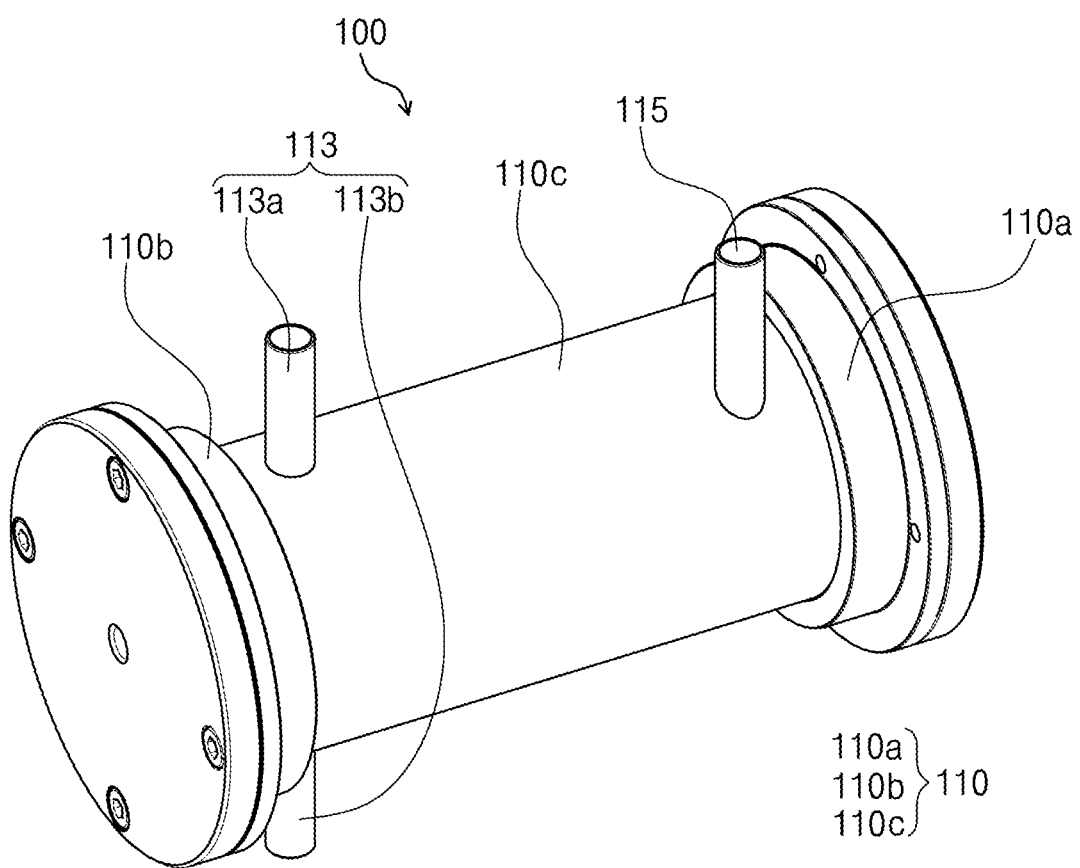
FIG. 1 is a perspective view of a fluid treatment module according to an embodiment of the present invention.

Hereinafter, embodiments of the present disclosure will be described with reference to the accompanying drawings. It should be understood that the embodiments are provided for complete disclosure and a thorough understanding of the present disclosure by those skilled in the art. Therefore, the present disclosure is not limited to the following embodiments and may be embodied in different ways. In addition, the drawings may be exaggerated in width, length, and thickness of components for descriptive convenience and clarity only. Like components will be denoted by like reference numerals throughout the specification.

Hereinafter, exemplary embodiments of the present invention will be described in detail with reference to the accompanying drawings so as to fully convey the spirit of the present invention to those skilled in the art.

Figure 2:
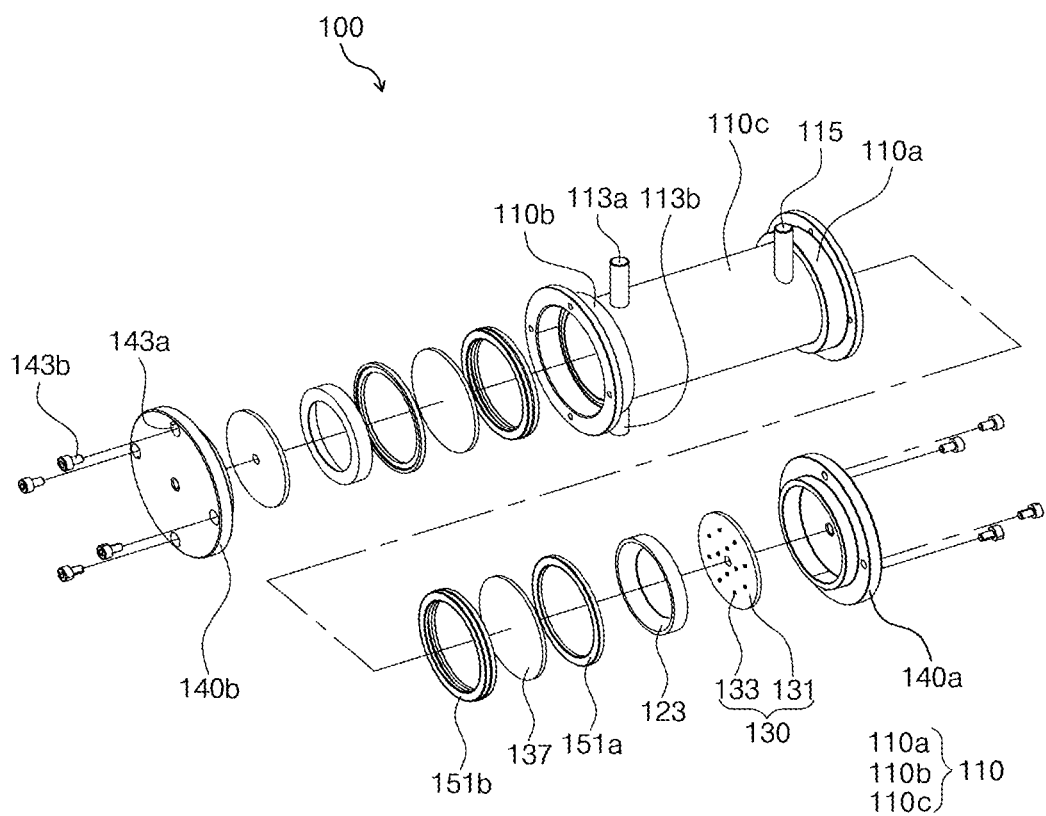
FIG. 2 is an exploded perspective view of the fluid treatment module according to the embodiment of the present invention.
Figure 3:
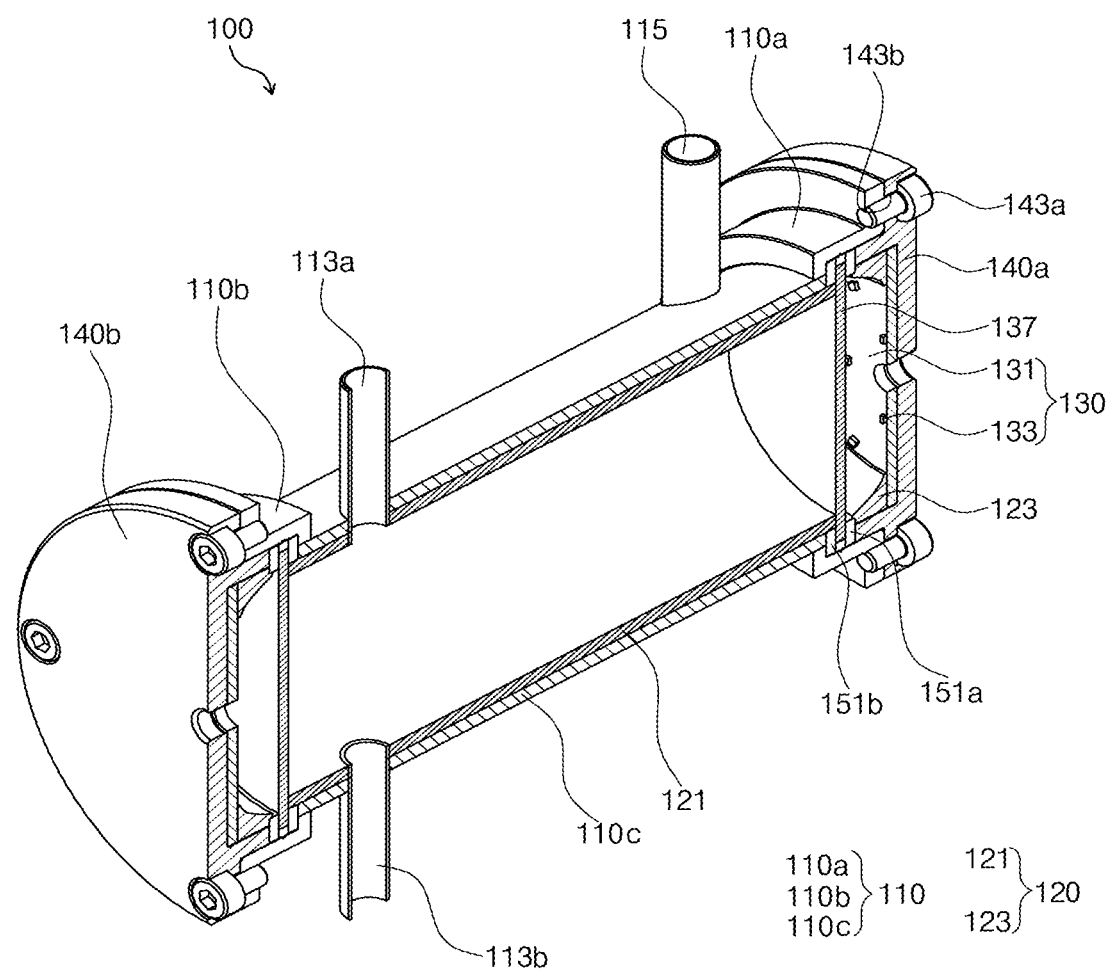
FIG. 3 is a perspective longitudinal sectional view of the fluid treatment module shown in FIG. 1.

FIG. 1 is a perspective view of a fluid treatment module according to an embodiment of the present invention and FIG. 2 is an exploded perspective view of the fluid treatment module according to the embodiment of the present invention. FIG. 3 is a perspective longitudinal sectional view of the fluid treatment module shown in FIG. 1.

One embodiment of the present invention relates to a fluid treatment module. In the embodiment, the term "fluid" refers to an object to be treated using the fluid treatment module and may include water (especially running water) or air. In one embodiment, treatment of the fluid includes, for example, sterilizing, purifying, and deodorizing the fluid through the fluid treatment module. However, treatment of the fluid is not limited thereto and may include other possible treatments carried out using the fluid treatment module described below.

Referring to FIG. 1 to FIG. 3, a fluid treatment module 100 according to one embodiment includes a pipe 110, in which fluid flows, and a light source module 130 emitting light towards the fluid in the pipe 110. The pipe 110 extends in one direction and has a shape open at opposite ends thereof. The pipe 110 may include a body 110c, which extends in a longitudinal direction thereof, and a first end 110a and a second end 110b disposed in the longitudinal direction of the body 110c. The body 110c has a hollow pipe shape having a predetermined diameter. The first end 110a and the second end 110b are connected to the opposite ends of the body 110c and may have the same diameter as or a larger diameter than the body 110c. The pipe 110 provides an interior space, that is, a flow channel, in which the fluid flows while being treated. Hereinafter, a direction in which the pipe 110 extends will be referred to as an extension direction of the pipe 110 or the longitudinal direction of the pipe 110.

In the embodiment, the pipe 110 may have a substantially cylindrical shape. In this case, a cross-section crossing a longitudinal direction of the cylindrical shape has a circular shape. However, it should be understood that the pipe 110 is not limited thereto and may have various cross-sectional shapes, for example, an elliptical shape, a rectangular shape, a semicircular shape, and the like.

The pipe 110 may be formed of a material having high reflectivity and/or a metal having high thermal conductivity. For example, the pipe 110 may be formed of a material having high reflectivity, such as stainless steel, aluminum, magnesium oxide, and the like, or may be formed of a material having high thermal conductivity, such as stainless steel, aluminum, silver, gold, copper, and alloys thereof. Metals having high thermal conductivity can effectively discharge heat from the pipe 110.

However, the pipe 110 is not limited thereto and may be formed of a material that transmits at least part of light emitted from the light source module 130 such that the light can reach the fluid inside the pipe 110, when the light source module 130 is disposed outside the pipe 110. The material capable of transmitting light may include various types of polymer resins, quartz, glass, and the like. For example, the entirety of the pipe 110 or a portion of the pipe 110 adjacent to the light source module 130 may be formed of a transparent material to allow the light emitted from the light source module 130 to reach the fluid.

The pipe 110 is provided with an inlet 113 through which the fluid enters the pipe 110 and an outlet 115 through which the fluid is discharged therefrom after treatment. The inlet 113 and/or the outlet 115 may be provided to at least one region of the pipe 110 selected from among the body 110c, the first end 110a, and the second end 110b.

As shown in FIG. 1 and FIG. 2, the inlet 113 is connected to the pipe 110. A connecting direction of the inlet 113 may be different from the extension direction of the pipe 110. In one embodiment, the connecting direction of the inlet 113 may be inclined or perpendicular to the extension direction of the pipe 110 such that the fluid enters the pipe 110 in a direction inclined or perpendicular thereto and flows in the extension direction of the pipe 110. The fluid flowing into the pipe 110 through inlet 113 is a fluid to be treated in the pipe 110, for example, an object that requires sterilization, purification, or deodorization treatment.

The outlet 115 may be disposed at a location separated from the inlet 113 and may be connected to the pipe 110. In one embodiment, a connecting direction of the outlet 115 may be inclined or perpendicular to the extension direction of the pipe 110 such that the fluid can be discharged from the pipe 110 in a direction inclined or perpendicular thereto after flowing in the extension direction of the pipe 110. The fluid discharged from the pipe 110 through the outlet 115 is a fluid treated in the pipe 110, for example, an object subjected to sterilization, purification, or deodorization treatment.

In one embodiment, when viewed in a direction perpendicular to the longitudinal direction of the pipe 110, the inlet 113 may be provided to at least one end side selected from among the opposite ends of the pipe 110 and the outlet 115 may also be provided to at least one end side selected from among the opposite ends of the pipe 110. In other words, in the embodiment, assuming the opposite ends of the pipe 110 in the longitudinal direction are referred to as the first end 110a and the second end 110b, respectively, each of the inlet 113 and the outlet 115 may be provided to at least one end side selected from among the first end 110a and the second end 110b or may be provided to both the first end 110a side and the second end 110b side. For example, as shown in the drawings, the inlet 113 may be provided to the first end 110a side and the outlet 115 may be provided to the second end 110b side. Alternatively, the inlet 113 may be provided to the second end 110b side and the outlet 115 may be provided to the first end 110a side. However, it should be understood that the locations of the inlet 113 and the outlet 115 are not limited thereto. For example, the inlet 113 and/or the outlet 115 may be disposed at a center of the pipe 110 instead of the opposite ends thereof.

Figure 4A:
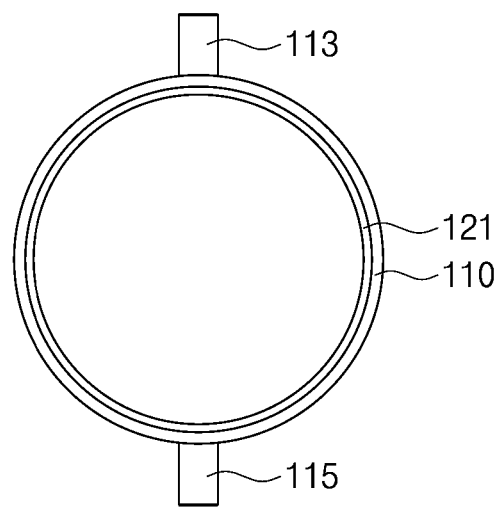
FIG. 4A is a sectional view of some components of the fluid treatment module according to the embodiment of the present invention, particularly illustrating a pipe, thereof.
Figure 4B:
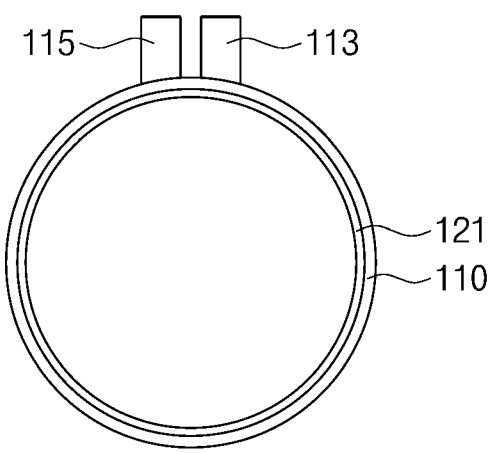
FIG. 4B is a sectional view of some components of the fluid treatment module according to the embodiment of the present invention, particularly illustrating an inlet thereof.
Figure 4C:
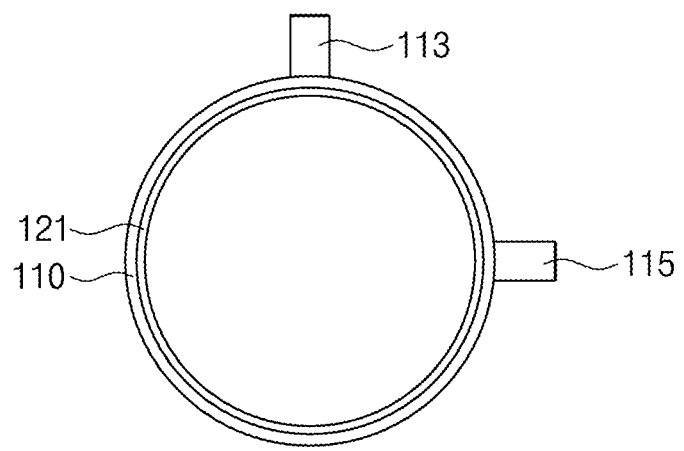
FIG. 4C is a sectional view of some components of the fluid treatment module according to the embodiment of the present invention, particularly illustrating an outlet thereof.

In the embodiment, the inlet 113 and the outlet 115 may be disposed in various ways when viewed in the longitudinal direction of the pipe 110. FIG. 4A to FIG. 4C are sectional views of some components of the fluid treatment module according to the embodiment of the present invention, particularly illustrating the pipe 110, the inlet 113, and the outlet 115, in which each of the inlet 113 and the outlet 115 is provided singularly. In FIG. 4A to FIG. 4C, reference numeral 121 indicates a first reflector.

Referring to FIG. 4A, the inlet 113 and the outlet 115 may be connected to the pipe 110 to face each other with the center of the pipe 110 disposed therebetween, when viewed in a cross-section perpendicular to the extension direction of the pipe 110. That is, the inlet 113 and the outlet 115 may be disposed at symmetric locations with the center of the pipe 110 disposed therebetween. However, it should be understood that the inlet 113 and the outlet 115 are not required to be completely symmetric about the center of the pipe 110. Referring to FIG. 4B, the inlet 113 and the outlet 115 may be connected to the pipe 110 at the same side with reference to the center of the pipe 110. In this case, as shown in the drawings, the inlet 113 and the outlet 115 may be separated from the pipe 110. That is, the inlet 113 and the outlet 115 may be collinearly or non-collinearly disposed in the extension direction of the pipe 110. Alternatively, the inlet 113 and the outlet 115 may be disposed to overlap each other. Referring to FIG. 4C, the inlet 113 and the outlet 115 may be connected to the pipe 110 to be perpendicular to each other.

The locations of the inlet 113 and the outlet 115 may be changed depending upon the kind of apparatus adopting the fluid treatment module. In particular, the locations of the inlet and the outlet may be set in various ways depending upon a fluid treatment amount or a degree of fluid sterilization required by the apparatus.

Although each of the inlet 113 and the outlet 115 is provided singularly in FIGS. 1-3, it should be understood that this structure is provided for illustration of a positional relationship between the inlet 113 and the outlet 115. Accordingly, when one of the inlet 113 and the outlet 115 is provided in plural, the inlets 113 or the outlets 115 may be individually disposed at different locations. For example, for the fluid treatment module including two inlets 113, that is, a first inlet 113a and a second inlet 113b, the first inlet 113a is disposed at a side opposite the outlet 115 and the second inlet 113b may be disposed at the same side as the outlet 115 when viewed in the extension direction of the pipe 110.

Referring again to FIG. 1 to FIG. 3, in the embodiment, the inlet 113 and the outlet 115 may have a circular or elliptical cross-section, without being limited thereto. Alternatively, the inlet 113 and the outlet 115 may have various shapes, for example, a polygonal shape. Here, the cross-section of each of the inlet 113 and the outlet 115 may be taken in the extension direction of the inlet 113 or in a direction crossing a direction in which the flow channel is formed.

Although not shown in the drawings, the inlet 113 and/or the outlet 115 may be provided with a separate pipe. The separate pipe may be connected to the inlet 113 and the outlet 115 through a nozzle. The nozzle may be coupled to the inlet 113 and/or the outlet 115 in various ways, for example, by screw coupling.

In one embodiment, the flow amount or speed of the fluid supplied through the inlet 113 and the flow amount or speed of the fluid discharged through the outlet 115 may be controlled depending upon the number and diameter of the inlets 113 and the outlets 115. To this end, in one embodiment, the inlet 113 and the outlet 115 may have the same diameter or different diameters. According to the embodiment, although the inlet 113 having the same diameter as the outlet 115 can provide good fluid treatment efficiency, the inlet 113 having a larger diameter than the outlet 115 can provide better fluid treatment efficiency.

Further, in one embodiment, at least one of the inlet 113 and the outlet 115 may be provided in plural. For example, the inlet 113 may be provided in plural and the outlet 115 may be provided singularly. Alternatively, the inlet 113 may be provided singularly and the outlet 115 may be provided in plural or both the inlet 113 and the outlet 115 may be provided in plural. For the fluid treatment device including multiple inlets 113 and multiple outlets 115, the inlets 113 and the outlets 115 may be provided in one-to-one correspondence. In particular, in one embodiment, the fluid treatment device including two inlets 113 and one outlet 115 can have improved fluid treatment efficiency.

Figure 5A:
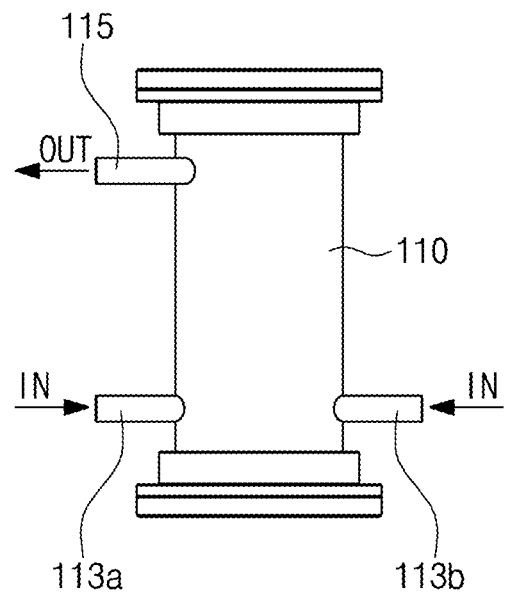
FIG. 5A is a side sectional view of the fluid treatment module according to the embodiment of the present invention, particularly illustrating the pipe thereof.
Figure 5B:
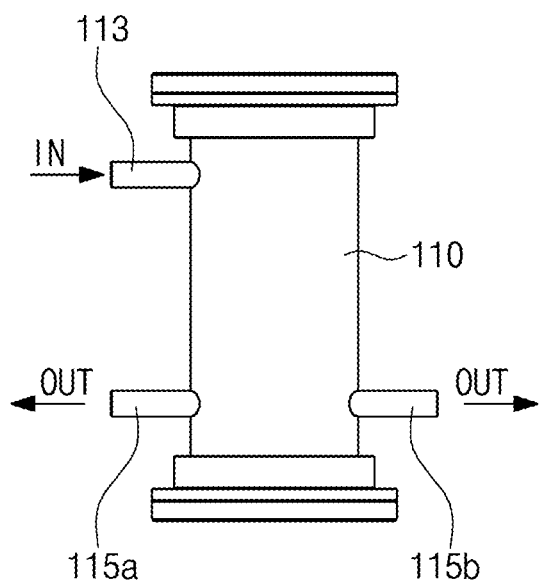
FIG. 5B is a side sectional view of the fluid treatment module according to the embodiment of the present invention, particularly illustrating the inlet thereof.
Figure 5C:
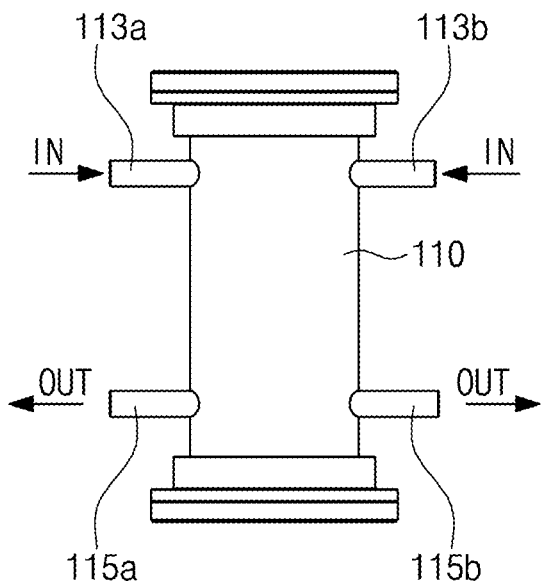
FIG. 5C is a side sectional view of the fluid treatment module according to the embodiment of the present invention, particularly illustrating the outlet thereof.

FIG. 5A to FIG. 5C are side sectional views of the fluid treatment module according to the embodiment of the present invention, particularly illustrating the pipe, the inlet and the outlet thereof.

In one embodiment, as shown in FIG. 5A to FIG. 5C, each of the inlet and the outlet may be provided in various numbers. For example, the fluid treatment module may include multiple inlets (that is, a first inlet 113a and a second inlet 113b) and a single outlet 115, as shown in FIG. 5A; a single inlet 113 and multiple outlets (that is, a first outlet 115a and a second outlet 115b), as shown in FIG. 5B; or multiple inlets (that is, a first inlet 113a and a second inlet 113b) and multiple outlets (that is, a first outlet 115a and a second outlet 115b), as shown in FIG. 5C.

Although two inlets and two outlets are illustrated by way of example, it should be understood that the present invention is not limited thereto, and a greater number of inlets or outlets may be provided.

Referring again to FIG. 1 to FIG. 3, for the fluid treatment module including two inlets 113 according to the embodiment, when viewed in the direction perpendicular to the extension direction of the pipe 110, the first and second inlets 113a, 113b may be provided to the second end 110b side and the outlet 115 may be provided to the first end 110a side, and when viewed in the extension direction of the pipe 110, the first inlet 113a may be disposed at an opposite side to the outlet 115, with the center of the pipe 110 disposed therebetween, and the second inlet 113b may be disposed at the same side as the outlet 115 with reference to the center of the pipe 110.

The fluid treatment effect depending upon the number and diameter of the inlets 113 and the outlets 115 will be described below.

The light source module 130 supplies light suitable for treatment of the fluid. The light source module 130 may be disposed at various locations adjacent to the fluid to emit light for treatment (for example, sterilization, purification, or deodorization) of the fluid.

The light source module 130 emits light and may be disposed at one side selected from among the first end 110a and the second end 110b of the pipe 110. In this embodiment, the light source module 130 is provided to both the first end 110a and the second end 110b by way of example. However, it should be understood that the location of the light source module 130 is not limited thereto and may be provided to one of the opposite ends of the pipe 110 in the longitudinal direction thereof. It should be understood that the location of the light source module 130 in this embodiment is provided for illustration only and is not to be construed in any way as limiting the present invention and that the light source module 130 may be disposed at any location so long as the light source module 130 can irradiate the interior of the pipe 10. Unlike in FIGS. 2-3, the light source module 130 may be disposed outside the pipe 110, without being limited thereto.

The light source module 130 may include a substrate 131 and a light emitting diode 133 mounted on the substrate 131. The substrate 131 may be provided in various forms, for example, in the form of a disk having a diameter corresponding to the pipe 10. Multiple light emitting diodes 133 may be arranged in a predetermined direction on the substrate 131. The substrate 31 may be provided with an opening through which a wire is connected to the light emitting diode 133 to supply power thereto.

For the light source module 130 including multiple light emitting diodes 133, the light emitting diodes 133 may emit light in the same wavelength band or in different wavelength bands. For example, in one embodiment, all of the light emitting diodes 133 may emit UV light having the same or similar wavelength. In another embodiment, some light emitting diodes 133 may emit light in some UV wavelength bands and the other light emitting diodes 133 may emit light in other UV wavelength bands.

When the light emitting diodes 133 emit light in different wavelength bands, the light emitting diodes 133 may be arranged in various sequences. For example, light emitting diodes 133 emitting light in a first wavelength band and light emitting diodes 133 emitting light in a second wavelength band different from the first wavelength band may be alternately arranged.

The light source module 130 may emit light in various wavelength bands. The light source module 130 may emit light in the visible spectrum, light in the UV spectrum, or light in other wavelength bands. In one embodiment, light emitted from the light source module 130 may have various wavelengths depending upon the type of fluid to be treated or the type of object to be treated (for example, germs, bacteria, and the like). In particular, when the fluid is to be sterilized, the light source module 130 may emit light having a germicidal wavelength. For example, the light source module 130 may emit light in the UV spectrum. In one embodiment, the light source module 130 may emit light in the wavelength band of about 100 nm to about 420 nm, which is germicidal to microorganisms. In one embodiment, the light source module 130 may emit light in the wavelength band of about 100 nm to about 280 nm. In another embodiment, the light source module 130 may emit light in the wavelength band of about 180 nm to about 280 nm. In a further embodiment, the light source module 130 may emit light in the wavelength band of about 250 nm to about 260 nm. UV light in the above wavelength bands has high germicidal efficacy. For example, irradiation with UV light at an intensity of 100 μW/cm$^2$ can kill about 99% of bacteria, such as *Escherichia coli*, *Diphtheria bacillus*, and *Dysentery bacillus*. In addition, UV light in the above wavelength bands can kill bacteria that cause food poisoning, such as pathogenic *Escherichia coli*, *Staphylococcus aureus*, *Salmonella Weltevreden*, *S. Typhimurium*, *Enterococcus faecalis*, *Bacillus cereus*, *Pseudomonas aeruginosa*, *Vibrio parahaemolyticus*, *Listeria monocytogenes*, *Yersinia enterocolitica*, *Clostridium perfringens*, *Clostridium botulinum*, *Campylobacter jejuni*, or *Enterobacter sakazakii*.

In one embodiment, the light source module 130 may emit light having various wavelengths and at least part of the light source module 130 may include a material that causes a catalytic reaction in response to light emitted from the light source module 130. For example, a photocatalytic layer formed of a photocatalytic material may be disposed on the entirety or a portion of an inner surface and/or an outer surface of the pipe 10 according to the present invention. The photocatalytic layer may be disposed in any region so long as the light emitted from the light source module 130 can reach the region.

A photocatalyst refers to a material causing a catalytic reaction with light emitted from a light source. The photocatalyst can react with light in various wavelength bands depending on substances constituting the photocatalyst. In one embodiment, a material causing photocatalytic reaction with light in the UV wavelength band among various wavelength bands may be used. However, the photocatalyst is not limited thereto and other photocatalysts having the same or similar mechanism may be used depending on light emitted from the light source.

The photocatalyst is activated by UV light to cause chemical reaction, thereby decomposing various pollutants and bacteria in the fluid, which contacts the photocatalyst, through redox reaction.

Although not shown in FIGS. 1-3, the fluid treatment module 100 according to the embodiment may further include a drive circuit connected to the light source module 130 and an interconnect portion connecting the drive circuit to the light source module 130. The drive circuit may supply electric power to at least one light source module 130. For example, the drive circuit may be provided to the fluid treatment module 100 having two light source modules 130 to independently supply electric power to each of the light source modules 130. Accordingly, the light source modules 130 may be selectively driven such that all of the two light source modules 130 can be turned on or off, or one light source module 130 can be turned on, with the other light source module 130 turned off.

A transmissive window 137 may be further disposed between the light source module 130 and a fluid treatment space inside the pipe 110 to transmit light emitted from the light source module 130 to the interior of the pipe 110.

The transmissive window 137 serves to protect the substrate 131 and the light source and may be formed of a transparent, electrically insulating material. However, it should be understood that the present invention is not limited thereto and the transmissive window 137 may be formed of various other materials. For example, the transmissive window 37 may be formed of quartz or an organic polymer. Here, since the wavelength of light absorbed by/transmitted through the organic polymer depends on the type of monomers for the organic polymer, a method of forming the organic polymer, and conditions in which the organic polymer material is formed, the organic polymer may be selected in consideration of wavelengths of light emitted from the light sources. For example, organic polymers, such as poly (poly methyl methacrylate; PMMA), polyvinyl alcohol (PVA), polypropylene (PP), and low-density polyethylene (PE), absorb little or no UV light, whereas polymer resins such as polyester can absorb UV light.

In this embodiment, the substrate 131 and the transmissive window 137 may correspond to the pipe 110 in terms of shape and size.

A heat dissipation plate is disposed on an outer surface of the light source module 130 to dissipate heat generated from the light source module 130. In one embodiment, in a structure where the light source modules 130 are provided to the opposite ends of the pipe 110, a first heat dissipation plate 140a and a second heat dissipation plate 140b are disposed outside the two light source modules 130, respectively.

The first and second heat dissipation plates 140a, 140b are formed of a material having higher thermal conductivity than the substrate 131 of the light source module 130, and serve to discharge heat, which is generated from the light source module 130, particularly from the light emitting diode 133, and is transferred through the substrate 131. To this end, each of the first and second heat dissipation plates 140a, 140b directly contacts the rear surface of the substrate 131 of the light source module 130.

As the material having higher thermal conductivity than the substrate 131 of the light source module 130, various materials may be used. For the substrate 131 formed of a metal, each of the first and second heat dissipation plates 140a, 140b may be formed of a material having higher thermal conductivity than the metal constituting the substrate 131. For example, when the substrate 131 is formed of stainless steel, the first and second heat dissipation plates 140a, 140b may be formed of a metal, for example, aluminum, which has higher thermal conductivity than stainless steel. The material for the first and second heat dissipation plates 140a, 140b may be selected from among various materials so long as the first and second heat dissipation plates have higher thermal conductivity than the substrate 131, instead of being limited to a particular material.

In one embodiment, the first and second heat dissipation plates 140a, 140b may have a larger area than the substrate 131 to allow efficient dissipation of heat from the substrate 131. The substrate 131 is disposed inside the pipe 110 and may have a diameter corresponding to the pipe 110, and the first and second heat dissipation plates 140a, 140b may have a larger diameter than the substrate 131. In addition, each of the first and second heat dissipation plates 140a, 140b may have a larger diameter than the body 110c of the pipe 110. Since the first and second heat dissipation plates 140a, 140b may disposed at the opposite end sides of the pipe 110, that is, at the first and second ends 110a, 110b, the first and second heat dissipation plates 140a, 140b can be formed to protrude from the opposite ends of the pipe 110 and can be easily formed to have larger diameters.

In the embodiment, the first and second heat dissipation plates 140a, 140b enable easier dissipation of heat from a light source. As a result, the light source is prevented from being deteriorated due to heat from the light source, thereby providing a stable sterilization effect of the fluid treatment module 100 while improving reliability thereof.

In one embodiment, the fluid treatment module 100 may be provided with a reflector 120 in addition to the substrate 131 and the light emitting diodes 133 to improve fluid treatment efficiency by reflecting light emitted from the light emitting diodes 133 to travel inside the pipe 110.

The reflector 120 has higher reflectivity than the pipe 110. For example, when the pipe 110 is formed of a material, such as stainless steel, the reflector 120 is formed of a material having higher reflectivity than the stainless steel. In one embodiment, the reflector 120 formed of a material having higher reflectivity than the pipe 100 may be disposed inside the pipe 110 to increase reflectivity with respect to light traveling inside the pipe 110. Increase in reflectivity of light results in improvement in fluid treatment efficiency through efficient reflection of light inside the pipe 110.

The reflector 120 may be formed of a material that reflects light emitted from the light source module 130. The reflector 120 may be formed of a material reflecting 80% or more of light emitted from the light source module 130, and in one embodiment, 90% or more of the light in another embodiment, or 99% or more of the light in a further another embodiment.

The reflector 120 may be formed of a material having high reflectivity to maximize efficiency in extraction of light emitted from the light emitting diode chip 133. For example, the reflector 120 may be formed of a material having roughness to improve reflection and scattering of light on the surface thereof. Alternatively, the reflector 120 may be formed of a material having a porous surface. Although there are various porous materials having surface roughness, the reflector according to one embodiment may be formed of a polymer resin, for example, PTFE. However, it should be understood that the reflector 120 is not limited thereto and may be formed of other materials so long as the reflector 120 can secure sufficient reflectivity. For example, the reflector 120 may be formed of aluminum and/or an aluminum alloy. Alternatively, the reflector 120 may be formed of a material having high reflectivity, for example, various metals, such as silver, gold, tin, copper, chromium, nickel, molybdenum, titanium, and the like, and/or alloys thereof.

The reflector 120 may include a first reflector 121 disposed inside the pipe 110 and a second reflector 123 disposed near the light source module 130. The first reflector 121 and the second reflector 123 may be formed of the same material or different materials. For example, both the first reflector 121 and the second reflector 123 may be formed of polytetrafluoroethylene (PTFE). Alternatively, the first reflector 121 may be formed of PTFE and the second reflector 123 may be formed of an aluminum alloy.

The first reflector 121 covers the inner surface of the pipe 110. For the pipe 110 having a cylindrical shape, the first reflector 121 may be formed to cover the entirety of a cylindrical inner wall of the pipe 110. Here, the first reflector 121 may be present or absent on portions of the inner wall of the pipe 110 corresponding to the inlet 113 and the outlet 115. In the embodiment, the inner wall of the pipe 110 may be substantially prevented from being exposed by the first reflector 121, which is disposed on the inner wall of the pipe 110 so as to cover a light reaching region as much as possible.

The second reflector 123 is disposed on the substrate 131 along the periphery of a mounting region of the light emitting diodes 133. The second reflector 123 serves to reflect light emitted from the light emitting diodes 133 to travel toward each region in the pipe 110. To this end, the second reflector 123 has an opening exposing the mounting region of the light emitting diodes 133 and is disposed on the substrate 131 in a ring shape penetrated through upper and lower portions thereof.

According to one embodiment, the second reflector 123 may have an inner surface facing the opening, an outer surface facing the outside, and a bottom surface adjoining an upper surface of the substrate 131. The inner surface is at least partially inclined with respect to the upper surface of the substrate 131. With this structure, the opening of the second reflector 123 has a width gradually increasing from the upper surface of the substrate 131 in an upward direction. In other words, the second reflector 123 has an inner diameter gradually increasing from the upper surface of the substrate 131 in the upward direction. In a cross-section of the second reflector 123, an inclined side may be linear or curved and may have an inclination set at various angles in consideration of the number of light emitting diodes 133, a beam angle of the light emitting diode 133, and the intensity of light emitted from the light emitting diode 133, and the like.

The fluid treatment module 100 according to this embodiment may be provided with one or more sealing members 151a, 151b to tightly fasten the pipe 10 to the first and second heat dissipation plates 140a, 140b while preventing the fluid from leaking out of the fluid treatment module 100.

In one embodiment, the sealing members 151a, 151b may be disposed near a fluid treatment space, for example, between a first cap and the first end 110a of the pipe 110 and between a second cap and the second end 110b of the pipe 110, respectively. The first cap and the second cap will be further described below. Each of the sealing members 151a, 151b may include first and second sealing members 150a, 150b disposed between the substrate 131 and the transmissive window 137 and between the transmissive window 137 and a stepped portion inside the pipe 110, respectively. The first and second sealing members 150a, 150b serve to tightly fasten the pipe 110 to the first and second caps while preventing the fluid in a first space from leaking out through a gap between the pipe 110 and the first and second caps. For example, the first and the second sealing members 150a, 150b separate the fluid treatment space from the light source module 130 to prevent the light source module 130 from being damaged by the fluid. Each of the sealing members 151a, 151b may be provided singularly or in plural.

Each of the sealing members 151a, 151b has a closed cross-section so as to tightly fasten an inner region and an outer region of the pipe 110 to each other and to isolate and seal these regions from each other when the first and second caps are fastened to the pipe 110. For example, each of the first and second sealing members 150a, 150b may be provided in the form of an O-ring.

The sealing members 151a, 151b may be formed of a soft elastic material. When the sealing members 151a, 151b are formed of such an elastic material, the sealing members 151a, 151b can be compressed against the pipe 110 upon fastening the pipe 110 to the first and second heat dissipation plates 140a, 140b, thereby maintaining a tight fastening structure.

Although the elastic material forming the sealing members 151a, 151b may include a silicone resin, it will be understood that the present invention is not limited thereto and the sealing members 151a, 151b may be formed of any other suitable material. For example, natural or synthetic rubber or other elastic organic polymers may be used as the elastic material.

In one embodiment, the first and second heat dissipation plates 140a, 140b may be used as first and second caps encapsulating the first and second ends 110a, 110b of the pipe 110, respectively. Accordingly, in this embodiment, each of the first and second heat dissipation plates 140a, 140b may have a fastening portion coupled to the pipe 110.

The fastening portion may be provided in various forms. For example, as the fastening portion, each of the first and second heat dissipation plates 140a, 140b may have an insertion portion, which has a diameter corresponding to the inner diameter of the pipe 110 and is inserted into an end of the pipe 110 to encapsulate the pipe 110.

In one embodiment, the first heat dissipation plate 140a is disposed at the first end 110a of the pipe 110 to be fastened to the pipe 110. The first heat dissipation plate 140a is formed with stepped portions having different outer diameters to be inserted into and fastened to the pipe 110. For example, a portion of the first heat dissipation plate 140a facing the first end 110a of the pipe 110 has an outer diameter corresponding to the inner diameter of the pipe 110.

In one embodiment, the pipe 110 and the first heat dissipation plate 140a may be provided with fastening members for coupling the pipe 110 to the first heat dissipation plate 140a. For example, the pipe 110 and the first heat dissipation plate 140a may be provided with fastening holes 143a such that the pipe 110 can be coupled to the first heat dissipation plate 140a by coupling fastening bolts 143b to the fastening holes 143a of the pipe 110 and the first heat dissipation plate 140a.

The second heat dissipation plate 140b is provided to the second end 110b of the pipe 110 to be fastened to the pipe 110. The second heat dissipation plate 140b may be also formed with stepped portions having different outer diameters and may be inserted into and fastened to the pipe 110 in the same manner as the first heat dissipation plate 140a.

Likewise, the pipe 110 and the second heat dissipation plate 140b may be provided with fastening members for coupling the pipe 110 to the second heat dissipation plate 140b. For example, the pipe 110 and the second heat dissipation plate 140b may be provided with fastening holes 143a such that the pipe 110 can be coupled to the second heat dissipation plate 140b by coupling fastening bolts 143b to the fastening holes 143a of the pipe 110 and the second heat dissipation plate 140b.

In one embodiment, the first and second heat dissipation plates 140a, 140b are used not only as heat dissipation members for dissipation of heat generated from the light source module 130, but also as tools for encapsulating the pipe 110, that is, as the first and second caps. Alternatively, encapsulating members for encapsulating the pipe 110 may be further provided as separate components from the first and second heat dissipation plates 140a, 140b. In this case, the separate encapsulating members may also be formed of a material having high thermal conductivity to allow efficient dissipation of heat from the first and second heat dissipation plates 140a, 140b.

In the fluid treatment module with the above structure, as the fluid flows in the extension direction of the pipe, the fluid is subjected to treatment, such as sterilization and the like, through exposure to light emitted from the light source module. The fluid treatment module according to the embodiments achieves remarkable improvement in fluid treatment efficiency through control of the number and diameter of the inlets and the outlets while improving treatment efficiency with light through the reflector. In addition, the fluid treatment module adopts the heat dissipation plate, thereby improving reliability of the light source module.

The fluid treatment module according to the embodiments of the present invention may be modified in various shapes without departing from the concept of the present invention.

Figure 6:
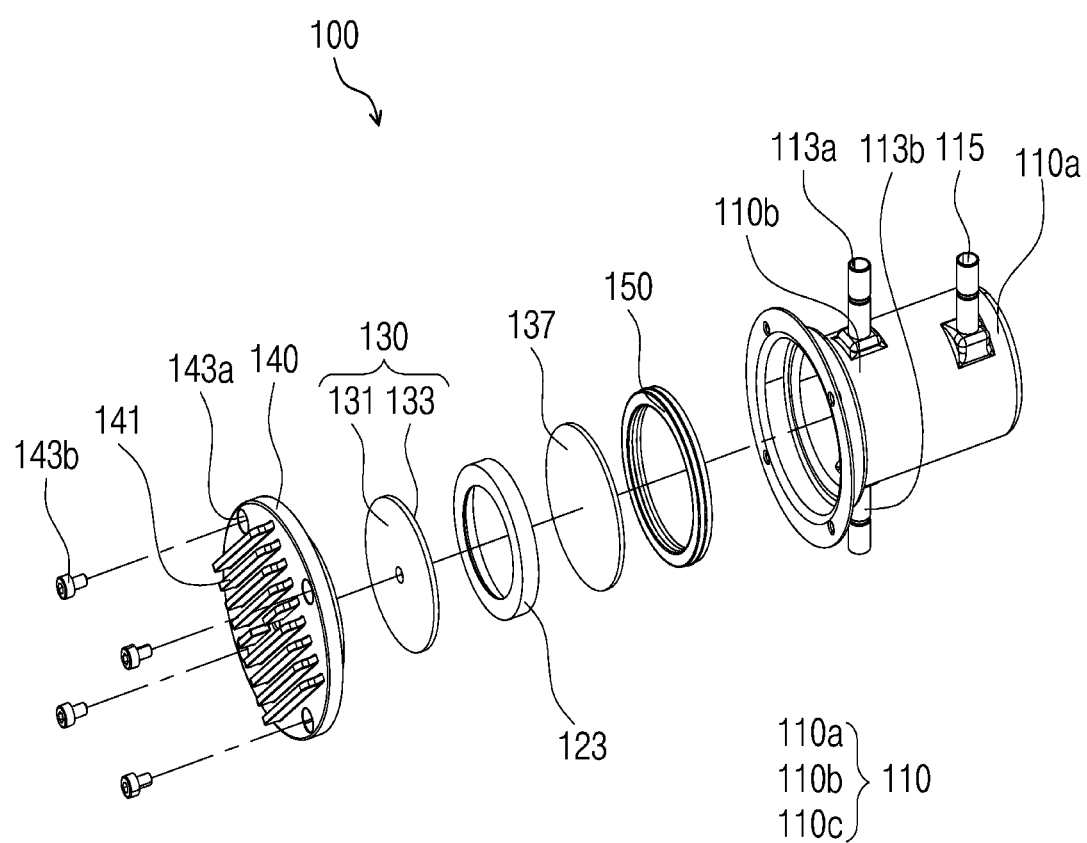
FIG. 6 is an exploded perspective view of a fluid treatment module according to an embodiment of the present invention.
Figure 7:
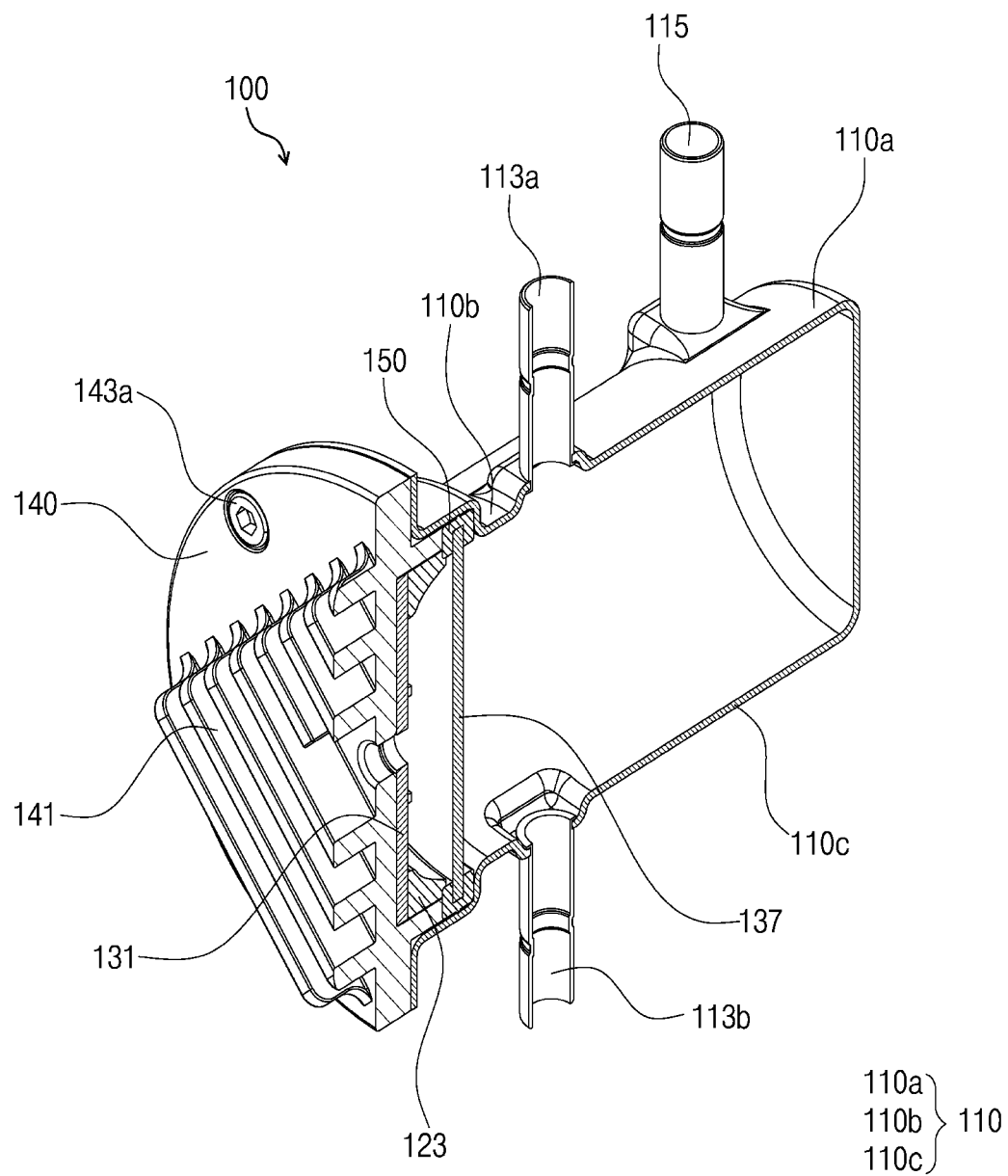
FIG. 7 is a perspective longitudinal sectional view of the fluid treatment module according to the embodiment of the present invention.

FIG. 6 is an exploded perspective view of a fluid treatment module according to an embodiment of the present invention and FIG. 7 is a perspective longitudinal sectional view of the fluid treatment module according to the embodiment of the present invention. The following description will focus on different features from the above embodiments to avoid repetition of description.

Referring to FIG. 6 and FIG. 7, a fluid treatment module 100 according to the embodiment includes a pipe 110, in which fluid flows, and a light source module 130 emitting light towards the fluid in the pipe 110. The pipe 110 extends in one direction and has a shape closed at one end thereof and open at the other end thereof. For the pipe 110 including a body 110c extending in a longitudinal direction thereof and a first end 110a and a second end 110b disposed in the longitudinal direction of the body 110c, the first end 110a has a closed shape having no inlet and the second end 110b has an open shape.

The pipe 110 is provided with an inlet 113 through which the fluid enters the pipe 110 and an outlet 115 through which the fluid is discharged therefrom after treatment. In this embodiment, the inlet 113 may be provided to an open-end side, that is, to the second end 110b side, and the outlet 115 may be provided to a closed end side, that is, to the first end 110a side.

In this embodiment, the inlet 113 may be provided in plural, for example, as a first inlet 113a and a second inlet 113b. In this embodiment, both the first inlet 113a and the second inlet 113b may be provided to the second end 110b side.

In this embodiment, the flow amount or speed of the fluid supplied through the inlet 113 and the flow amount or speed of the fluid discharged through the outlet 115 may be controlled depending upon the number and diameter of the inlets 113 and the outlets 115, as in the above embodiment.

The light source module 130 supplies light suitable for treatment of the fluid. In this embodiment, the light source module 130 may be disposed at the second end 110b side among the first end 110a and the second end 110b of the pipe 110. The light source module 130 is not disposed at the first end 110a side, which does not include an opening. The light source module 130 may include a substrate 131 and a light emitting diode 133 mounted on the substrate 131.

A transmissive window 137 may be further disposed between the light source module 130 and a fluid treatment space inside the pipe 110 to transmit light emitted from the light source module 130 to the interior of the pipe 110.

A heat dissipation plate 140 is disposed at an open-end side of the light source module 130 to dissipate heat generated from the light source module 130. In a structure where the light source module 130 is provided to the second end 110b of the pipe 110, the heat dissipation plate 140 is provided at the second end 110b side.

The heat dissipation plate 140 is formed of a material having higher thermal conductivity than the substrate 131 of the light source module 130, and serves to discharge heat, which is generated from the light source module 130, particularly from the light emitting diode 133, and is transferred through the substrate 131. To this end, the heat dissipation plate 140 directly contacts the rear surface of the substrate 131 of the light source module 130.

In one embodiment, the heat dissipation plate 140 may have a larger area than the substrate 131 to allow efficient dissipation of heat from the substrate 131. The substrate 131 is disposed inside the pipe 110 and may have a diameter corresponding to the pipe 110, and the heat dissipation plate 140 may have a larger diameter than the substrate 131. In addition, the heat dissipation plate 140 may have a larger diameter than the body 110c of the pipe 110. Since the heat dissipation plate 140 may disposed at the second end 110b of the pipe 110, the heat dissipation plate 140 can be formed to protrude from the second end 110b of the pipe 110 and can be easily formed to have a larger diameter.

Further, the heat dissipation plate 140 may include a protrusion 141 protruding from a surface thereof to allow easy dissipation of heat as much as possible. The protrusion 141 may be provided in plural, whereby the surface area of the heat dissipation plate 140 can be remarkably increased thereby, as compared with the heat dissipation plate 140 not including the protrusions 141. As the surface area of the heat dissipation plate 140 is increased, a contact area between the heat dissipation plate 140 and external air is increased, thereby enabling efficient dissipation of heat from the heat dissipation plate 140. In one embodiment, the protrusions 141 have a plate shape extending in one direction and may be spaced apart from each other. However, it should be understood that the protrusions 141 are not limited thereto and may have any shape without limitation so long as the protrusions can increase the surface area of the heat dissipation plate 140.

In this embodiment, the heat dissipation plate 140 including the protrusions 141 may be provided as an integrated structure. With this structure, the heat dissipation plate 140 may allow easier heat transfer than a structure where the heat dissipation plate 140 is not integrally formed therewith.

In the embodiment, the heat dissipation plate 140 enables easier dissipation of heat from a light source. As a result, the light source is prevented from being deteriorated due to heat from the light source, thereby providing a stable sterilization effect of the fluid treatment module 100 while improving reliability thereof.

In this embodiment, since the body 110c is blocked at the first end 110a thereof and the fluid enters the pipe through one side of the pipe and is discharged from the pipe through the other side thereof, an eddy can be easily generated at a blocked portion inside the body 110c. A time that the fluid stays in the body 100c is increased by the eddy. As a result, the exposure time of the fluid to light emitted from the light source module 130 is sufficiently increased and the fluid treatment effect is also finally improved.

As the time that the fluid stays in the body 100*c* is increased by the eddy, treatment efficiency with light is also improved. That is, since the fluid is irradiated with a sufficient quantity of light, a sufficient fluid treatment effect can be obtained even when the light source module 130 is disposed at one side in this embodiment. In addition, since the fluid is irradiated with a sufficient quantity of light, the body 110*c* may have a shorter length than the body according to the above embodiment. When the body 110*c* has a short distance, an eddy can be more easily generated inside the body 110*c*.

Furthermore, with improvement in treatment efficiency with light, the fluid treatment module 100 according to this embodiment can omit a reflector reflecting light to travel inside the pipe 110, for example, the reflector surrounding the inner wall of the pipe 110, unlike the above embodiment. In this embodiment, the reflector 120 does not include the first reflector 121 (see FIG. 2 and FIG. 3) inside the pipe 110 and may include the second reflector 123 disposed near the light source module 130. Here, the second reflector 123 is disposed on the substrate 131 along the periphery of the mounting region of the light emitting diodes 133. The second reflector 123, the light emitting diode 133 has an opening exposing the mounting region of the light emitting diodes 133 and is disposed on the substrate 131 in a ring shape penetrated through upper and lower portions thereof.

The fluid treatment module 100 according to this embodiment may be provided with a sealing member to tightly fasten the pipe 10 to the heat dissipation plate 140 while preventing the fluid from leaking out of the fluid treatment module.

Although the fluid treatment module 100 according to the embodiment shown in FIG. 2 and FIG. 3 is provided with two sealing members, the fluid treatment module 100 according to this embodiment may be provided with a single sealing member. In this embodiment, the sealing member 150 is disposed near the fluid treatment space while surrounding an end of the transmissive window 137 in an angled-C shape.

In the embodiment, the heat dissipation plate 140 may be used as a cap encapsulating the second end 110*b* of the pipe 110. Accordingly, in this embodiment, the heat dissipation plate 140 may have a fastening portion coupled to the pipe 110.

The fastening portion may be provided in various forms. For example, as the fastening portion, the heat dissipation plate 140 may have an insertion portion, which has a diameter corresponding to the inner diameter of the pipe 110 and is inserted into an end of the pipe 110 to encapsulate the pipe 110.

In the embodiment, the heat dissipation plate 140 is disposed at the second end 110*b* of the pipe 110 to be fastened to the pipe 110. The heat dissipation plate 14 is formed with stepped portions having different outer diameters to be inserted into and fastened to the pipe 110. For example, a portion of the heat dissipation plate 140 facing the second end 110*b* of the pipe 110 has an outer diameter corresponding to the inner diameter of the pipe 110.

In the embodiment, the pipe 110 and the heat dissipation plate 140 may be provided with fastening members for coupling the pipe 110 to the heat dissipation plate 140.

In one embodiment, the heat dissipation plate 140 is used not only as a heat dissipation member for dissipation of heat generated from the light source module 130, but also as a tool for encapsulating the pipe 110, that is, as a cap. Alternatively, an encapsulating member for encapsulating the pipe 110 may be further provided as a separate component from the heat dissipation plate 140. In this case, the separate encapsulating member may also be formed of a material having high thermal conductivity to allow efficient dissipation of heat from the heat dissipation plate 140.

In the fluid treatment module with the above structure, the body has a short length, thereby enabling reduction in overall size thereof. In addition, the fluid treatment module secures sufficient sterilization through generation of an eddy to increase the time that the fluid stays inside the body, thereby enabling reduction in the number of light source modules and the number of light emitting diodes. As a result, the number of light source modules and the number of light emitting diodes in each light source module are reduced, thereby reducing manufacturing costs and the number of manufacturing processes, such as a process of waterproofing the opposite ends of the body or a process of assembling the heat dissipation plate.

Figure 8A:
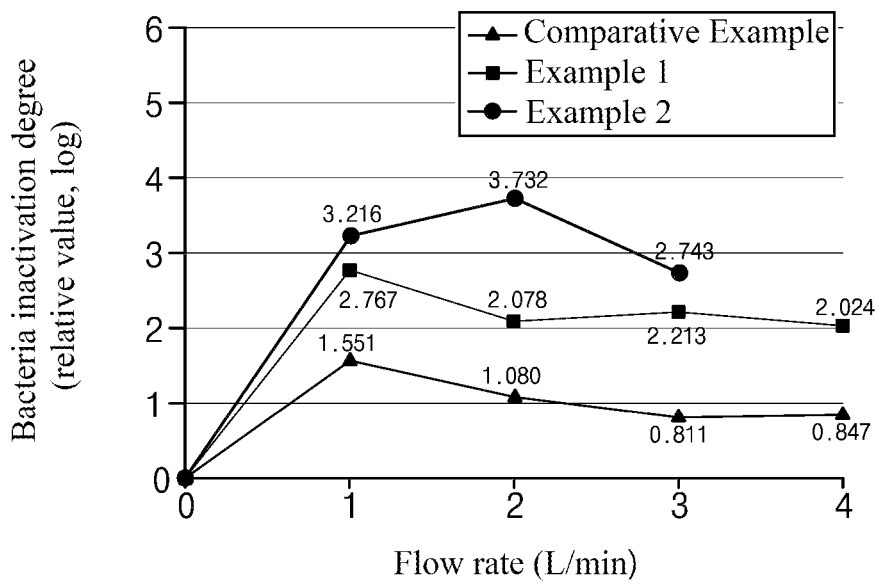
FIG. 8A is a graph depicting a fluid treatment effect depending upon the presence of a reflector with respect to Examples 1 and 2.
Figure 8B:
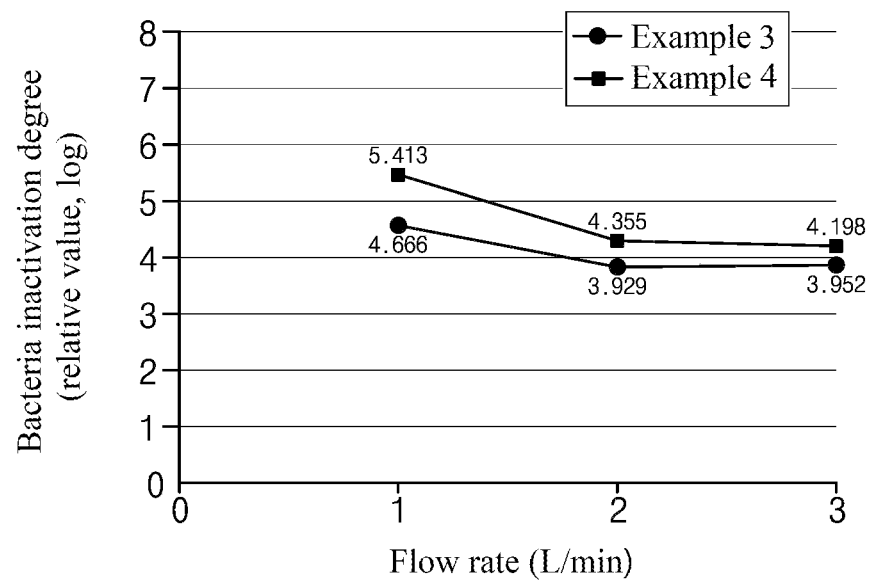
FIG. 8B is a graph depicting a fluid treatment effect depending upon the presence of a reflector with respect to Examples 3 and 4.
Figure 8C:
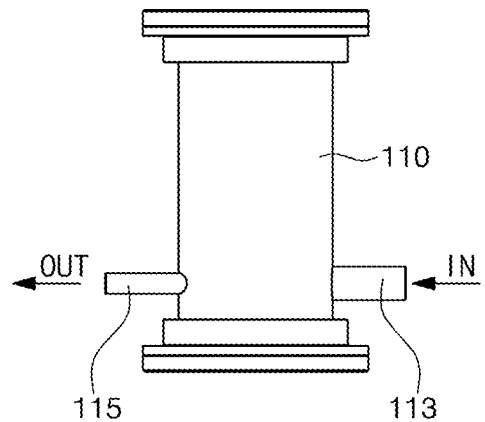
FIG. 8C is a side sectional view of a fluid treatment module used in experiments of FIG. 8A and FIG. 8B.

FIG. 8A and FIG. 8B are graphs depicting a fluid treatment effect depending upon the presence of the reflector, and FIG. 8C is a side sectional view of a fluid treatment module used in experiments of FIG. 8A and FIG. 8B. In FIG. 8A, Comparative Example is a fluid treatment module including no reflector, that is, a fluid treatment module not including the first and second reflectors, Example 1 is a fluid treatment module including the second reflector, and Example 2 is a fluid treatment module including both the first and second reflectors. In FIG. 8B, Example 3 is a fluid treatment module including the first reflector and Example 4 is a fluid treatment module including the first and second reflectors.

In FIG. 8A and FIG. 8B, in order to monitor the fluid treatment effect depending upon the presence of the reflector, experiments were carried out under the same conditions other than the reflector while changing the flow rate of fluid. The fluid was water and *E. coli* was used as bacteria. A bacteria inactivation degree according to treatment of the fluid was represented by a log scale (log CFU/mL) and a higher log value indicates higher sterilization capability (for example, 3 log CFU/mL indicates a bacteria inactivation degree of 99.9%). In each of the fluid treatment modules, one inlet and one outlet were disposed at the same end side to face each other, and the diameter of the inlet was two times the diameter of the outlet.

Referring to FIG. 8A, as compared with Comparative Example, Example 1 and Example 2 exhibited much higher fluid treatment efficiency, that is, much higher sterilization efficiency. For example, in treatment of 1 LPM (liter per minute) of the fluid, Comparative Example had a sterilization efficiency of 1.551 (log CFU/mL), whereas Examples 1 and 2 had a sterilization efficiency of 2.767 (log CFU/mL) and a sterilization efficiency of 3.216 (log CFU/mL), respectively. Further, in treatment of 2 LPM, Comparative Example had a sterilization efficiency of 1.080 (log CFU/mL), whereas Examples 1 and 2 had a sterilization efficiency of 2.078 (log CFU/mL) and a sterilization efficiency of 3.732 (log CFU/mL), respectively. In particular, it could be seen that Example 2 including the first and second reflectors exhibited much higher sterilization efficiency than Example 1 including the second reflector.

Referring to FIG. 8B, Example 3 and Example 4 exhibited much higher fluid treatment efficiency, that is, much higher sterilization efficiency. For example, in treatment of 1 LPM (liter per minute) of the fluid, Examples 3 and 4 had a sterilization efficiency of 4.666 (log CFU/mL) and a sterilization efficiency of 5.413 (log CFU/mL), respectively. In particular, it could be seen that Example 4 including the first and second reflectors exhibited much higher sterilization efficiency than Example 3 including only the first reflector.

As such, the fluid treatment module according to the embodiment is provided with the reflector, thereby securing much better fluid treatment capability.

In the fluid treatment module according to the embodiment, the inlet and the outlet may be provided in various shapes in order to control the fluid flowing in the pipe. FIG. 9A to FIG. 9F are side views of fluid treatment modules each provided with an inlet and an outlet through various modifications, and FIG. 10A to FIG. 10F are graphs depicting fluid treatment effects (sterilization effects) of the fluid treatment modules shown in FIG. 9A to FIG. 9F, respectively.

In FIG. 9A to FIG. 9F and FIG. 10A to FIG. 10F, experiments were carried out under the same conditions other than the locations and diameters of the inlet and the outlet, in which the flow rate of the fluid was set to 1 LPM. In particular, the fluid treatment modules used in these experiments include the reflector. The fluid was water and *E. coli* was used as bacteria. A bacteria inactivation degree according to treatment of the fluid was represented by a log scale (log CFU/mL) and a higher log value indicates higher sterilization capability (for example, 3 log CFU/mL indicates a bacteria inactivation degree of 99.9%).

Figure 10A:
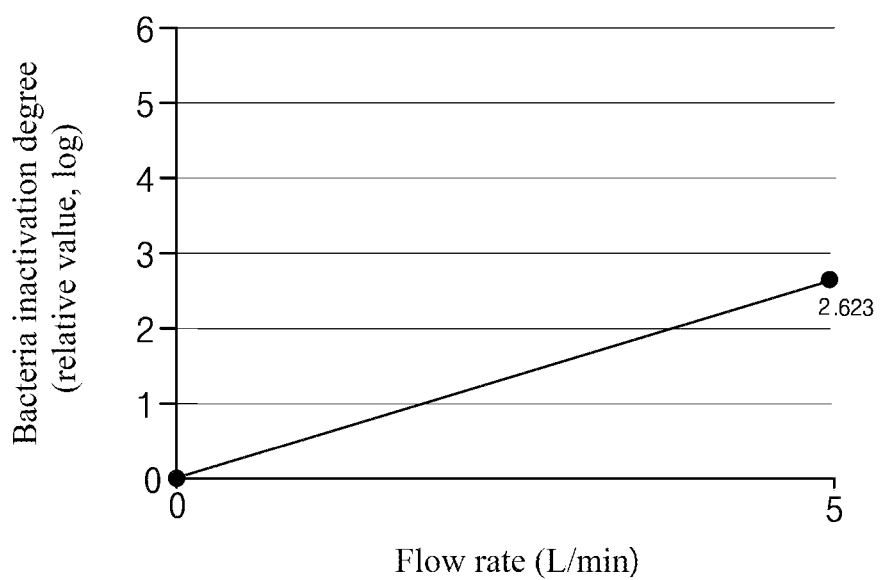
FIG. 10A is a graph depicting fluid treatment effects of the fluid treatment modules shown in FIG. 9A.
Figure 10B:
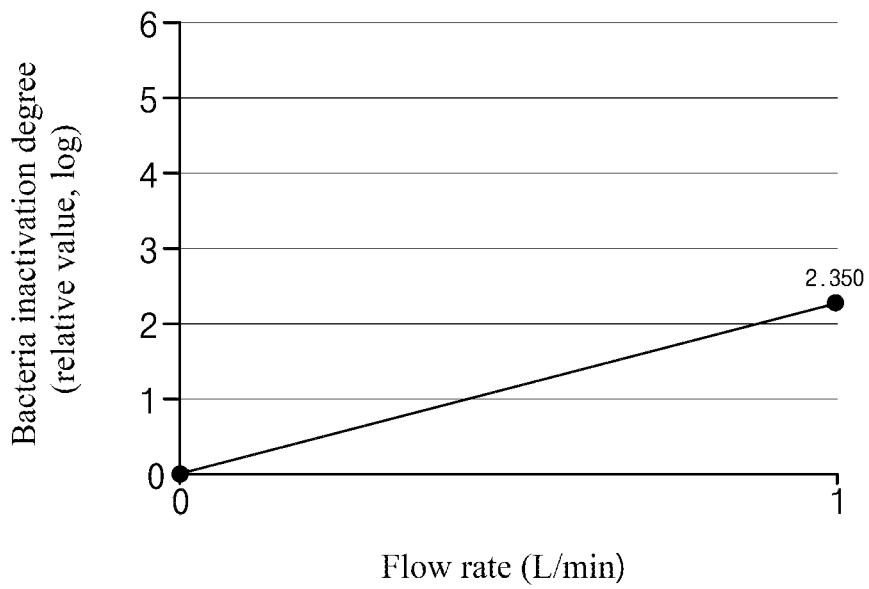
FIG. 10B is a graph depicting fluid treatment effects of the fluid treatment modules shown in FIG. 9B.

First, sterilization efficiency depending upon the diameter of each of the inlet and the outlet can be confirmed by comparing FIG. 10A with FIG. 10B.

FIG. 10A and FIG. 10B show graphs depicting fluid treatment effects of the fluid treatment modules each including one inlet and one outlet, in which FIG. 10A is a graph depicting the fluid treatment effect when the inlet and the outlet had the same diameter and FIG. 10B is a graph depicting the fluid treatment effect when the diameter of the outlet was ½ the diameter of the inlet.

Referring to FIG. 10A and FIG. 10B, the fluid treatment module including one inlet and one outlet having the same diameter exhibited a bacteria inactivation degree of 2.623 (log CFU/mL) at 1 LPM and the fluid treatment module including the inlet and the outlet having different diameters exhibited a bacteria inactivation degree of 2.350 (log CFU/mL) at 1 LPM. As such, when each of the inlet and the outlet was provided singularly, the fluid treatment module exhibited a bacteria inactivation degree of less than 3.000 (log CFU/mL), regardless of the diameter of each of the inlet and the outlet, and exhibited no significant difference in bacteria inactivation degree depending upon the diameter thereof.

Figure 10C:
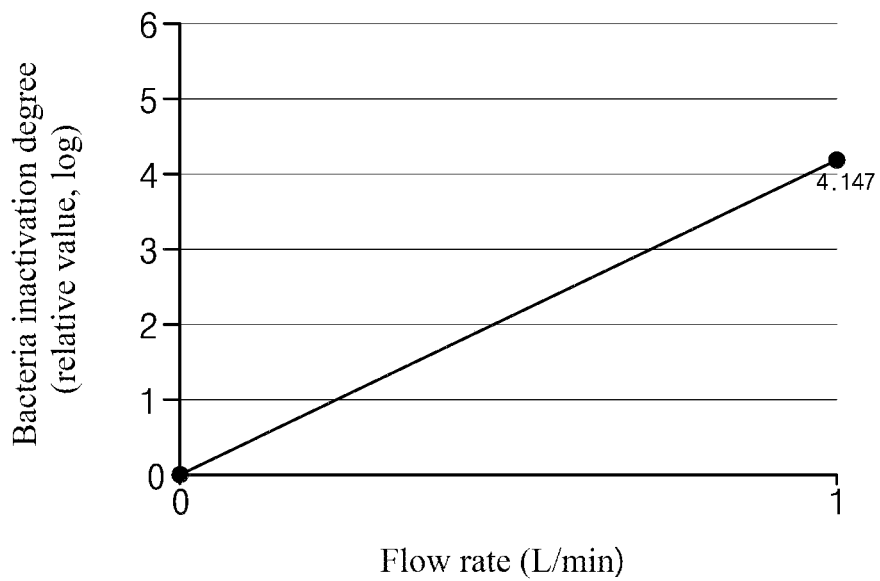
FIG. 10C is a graph depicting fluid treatment effects of the fluid treatment modules shown in FIG. 9C.

FIG. 10C is a graph depicting the fluid treatment effect of a fluid treatment module including two inlets (that is, a first inlet and a second inlet) and one outlet having the same diameter as the inlets.

Referring to FIG. 10C, the fluid treatment module including two inlets and one outlet each having the same diameter exhibited a bacteria inactivation degree of 4.147 (log CFU/mL) at 1 LPM. That is, it could be seen that increase in the number of inlets provided remarkable improvement in fluid treatment effect, that is, sterilization effect, as compared with the fluid treatment module including one inlet and one outlet.

It seemed that increase in the number of inlets through which the fluid flows into the pipe resulted in increase in frequency of exposure of the fluid to sterilizing light while maintaining the same flow rate by generating an eddy in the pipe, as compared with the comparative example in which the inlet was not further added. When the flow rate decreases, the frequency of exposure of the fluid to sterilizing light generally increases. However, according to the present invention, the sterilization effect can be improved while maintaining the flow rate at 1 LPM by controlling the number of inlets, as described above.

Figure 10D:
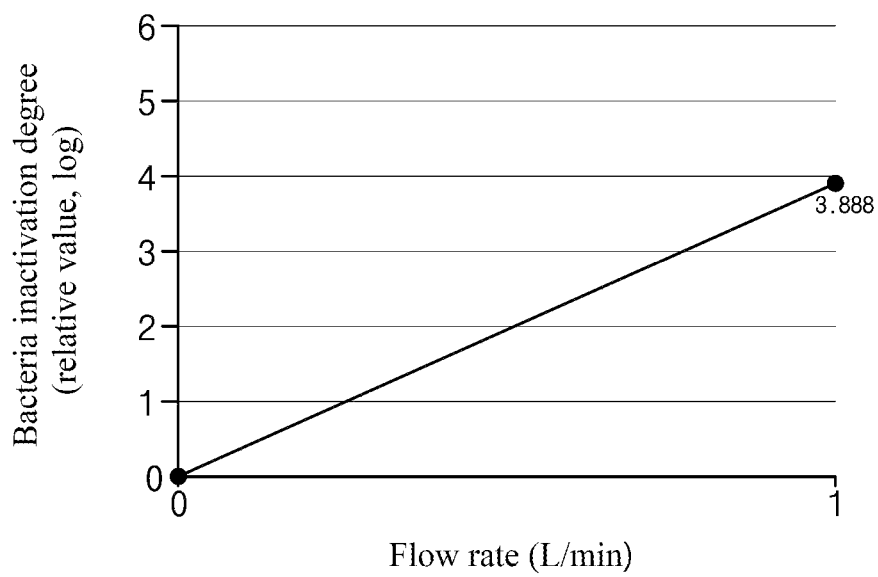
FIG. 10D is a graph depicting fluid treatment effects of the fluid treatment modules shown in FIG. 9D.
Figure 10E:
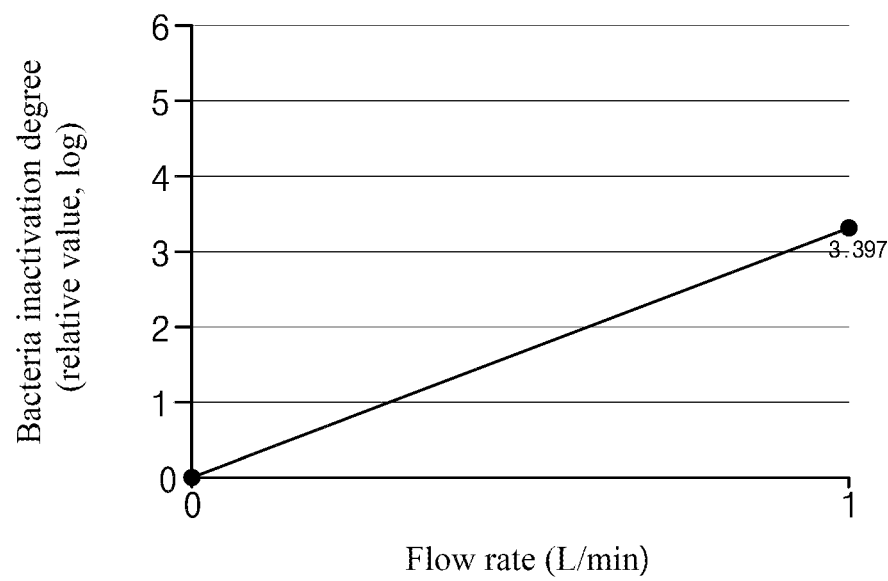
FIG. 10E is a graph depicting fluid treatment effects of the fluid treatment modules shown in FIG. 9E.

In one embodiment, sterilization efficiency of fluid treatment modules, in which the number of inlets is the same as the number of outlets and the inlet has a different diameter than the outlet, can be confirmed. FIG. 10D is a graph depicting the fluid treatment effect of a fluid treatment module in which the number of inlets and the number of outlets were the same as those in FIG. 10C and the diameter of the outlet was set to ½ the diameter of the inlet, and FIG. 10E is a graph depicting the fluid treatment effect of a fluid treatment module in which the number of inlets and the number of outlets were the same as those in FIG. 10C and the diameter of the inlet was set to ½ the diameter of the outlet. As a result, in FIG. 10D in which the diameter of the outlet was set to ½ the diameter of the inlet, the fluid treatment module exhibited a bacteria inactivation degree of 3.888 (log CFU/mL) at 1 LPM, and, in FIG. 10E in which the diameter of the inlet was set to ½ the diameter of the outlet, the fluid treatment module exhibited a bacteria inactivation degree of 3.897 (log CFU/mL) at 1 LPM.

Referring to FIG. 10C to FIG. 10E, it could be seen again that, regardless of difference in diameter between the inlet and the outlet, all of the fluid treatment modules exhibited a high sterilization power of 3 (log CFU/mL) (that is, a bacteria inactivation degree of 99.9%) and the fluid treatment efficiency remarkably increases with increasing number of inlets. In addition, it could be seen that the fluid treatment efficiency could be further improved through adjustment of the diameters of the inlet and the outlet in various ways, in particular, when the inlet and the outlet were formed to have the same diameter, as shown in FIG. 10C.

Figure 10F:
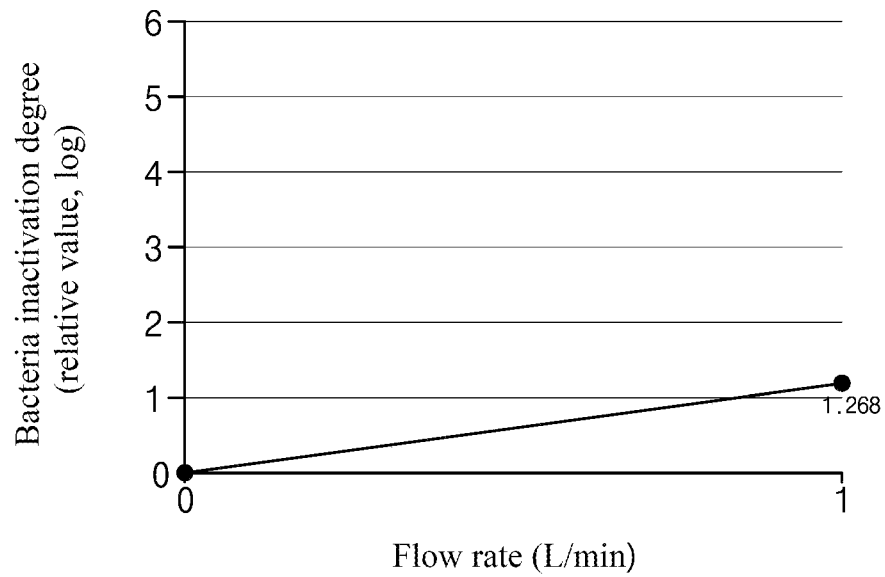
FIG. 10F is a graph depicting fluid treatment effects of the fluid treatment modules shown in FIG. 9F.

FIG. 10F is a graph depicting the fluid treatment effect of a fluid treatment module with different arrangement of the inlet and the outlet, in which the inlet and the outlet are disposed at the same end side, unlike the above experiment. Referring to FIG. 10F, the fluid treatment module, in which the inlet and the outlet are disposed at the same end side, exhibited a bacteria inactivation degree of 1.268 (log CFU/mL) at 1 LPM, thereby indicating significant deterioration in sterilization efficiency. It seemed that the arrangement of the inlet and the outlet at the same side increased the amount of the fluid discharged from the fluid treatment module instead of sufficiently staying in the pipe.

Figure 9A:
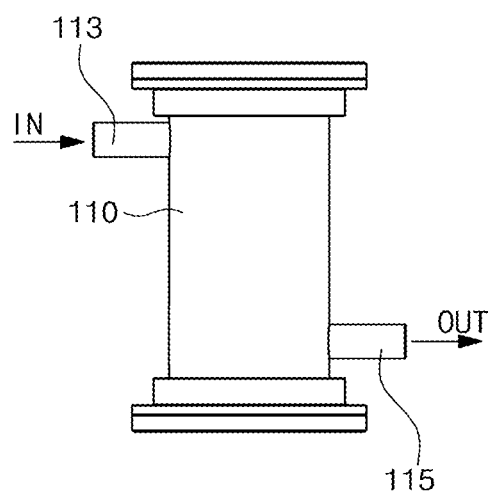
FIG. 9A is a side view of a fluid treatment module provided with an inlet and an outlet through a first modification.
Figure 9B:
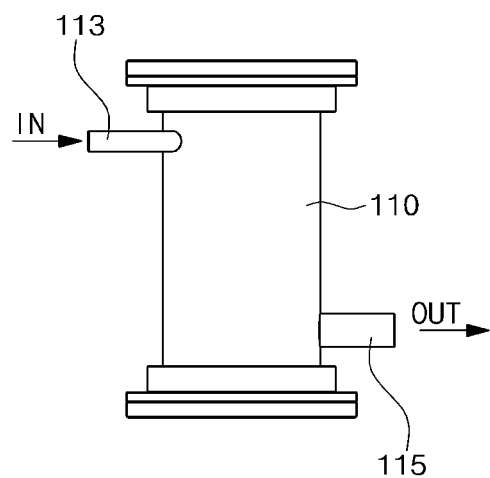
FIG. 9B is a side view of a fluid treatment module provided with an inlet and an outlet through a second modification.
Figure 9C:
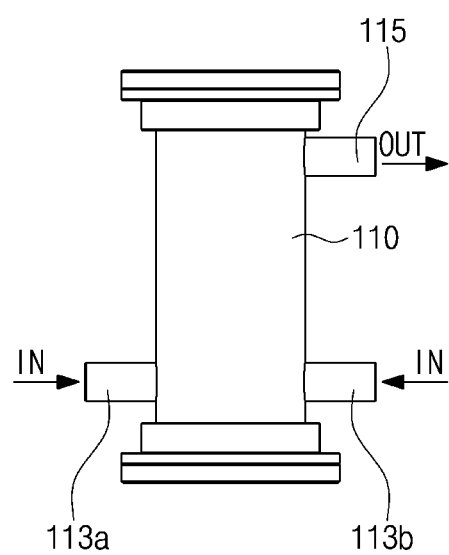
FIG. 9C is a side view of a fluid treatment module provided with an inlet and an outlet through a third modification.
Figure 9D:
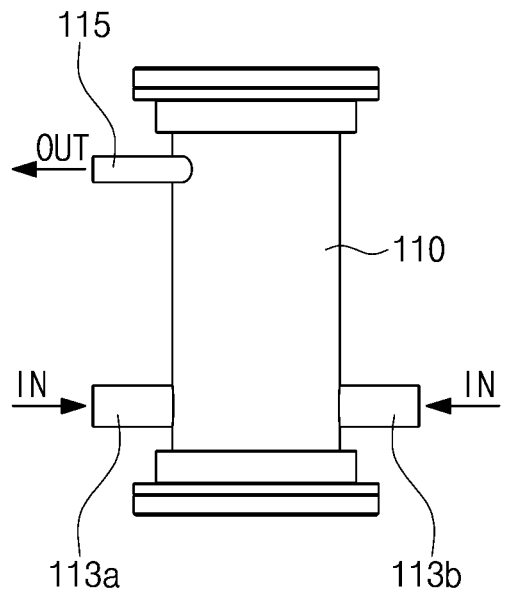
FIG. 9D is a side view of a fluid treatment module provided with an inlet and an outlet through a fourth modification.
Figure 9E:
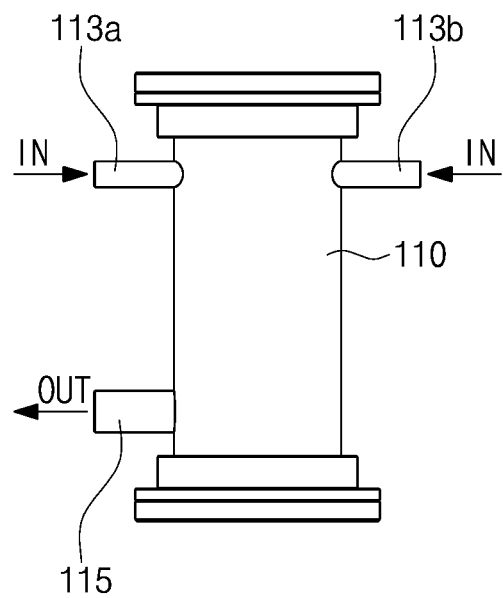
FIG. 9E is a side view of a fluid treatment module provided with an inlet and an outlet through a fifth modification.
Figure 9F:
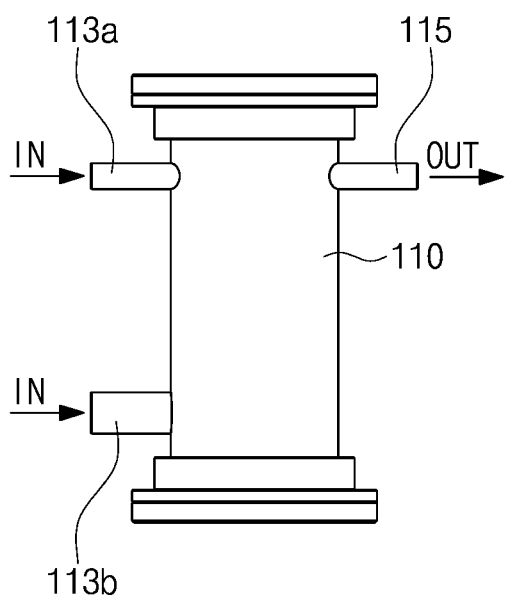
FIG. 9F is a side view of a fluid treatment module provided with an inlet and an outlet through a sixth modification.
Figure 11:
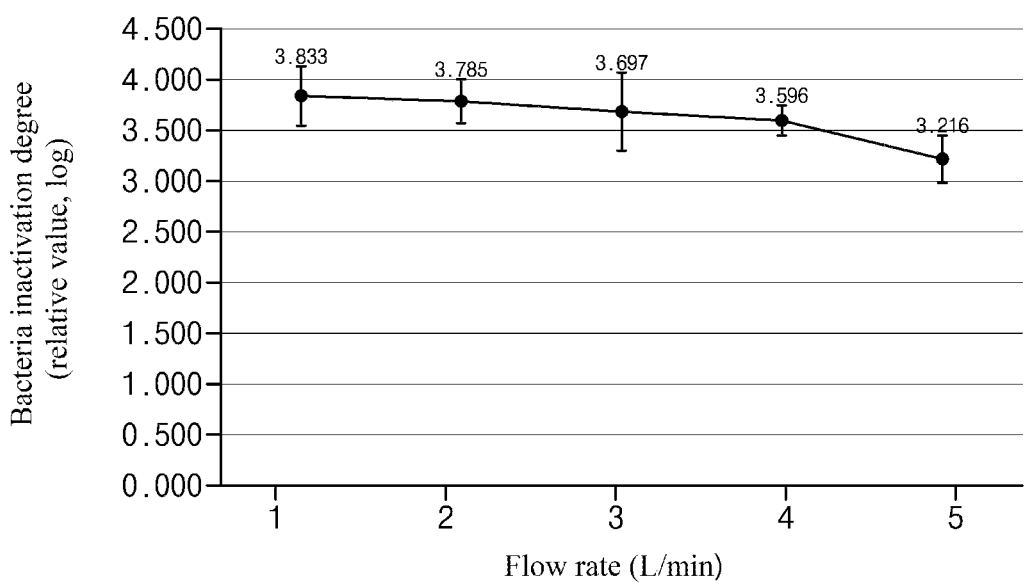
FIG. 11 is a graph depicting sterilization efficiency depending upon a flow rate of a fluid flowing in the pipe of the fluid treatment module according to the embodiment of the present invention.
Figure 12A:
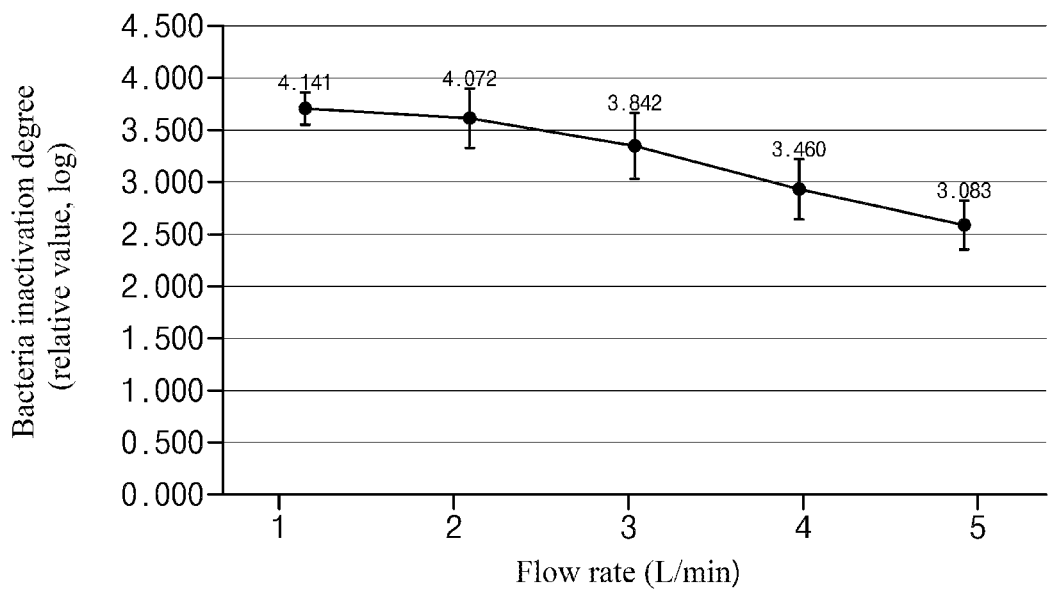
FIG. 12A is a graph depicting sterilization efficiency depending upon the flow rate of the fluid flowing in the pipe of the fluid treatment module according to the embodiment of the present invention.
Figure 12B:
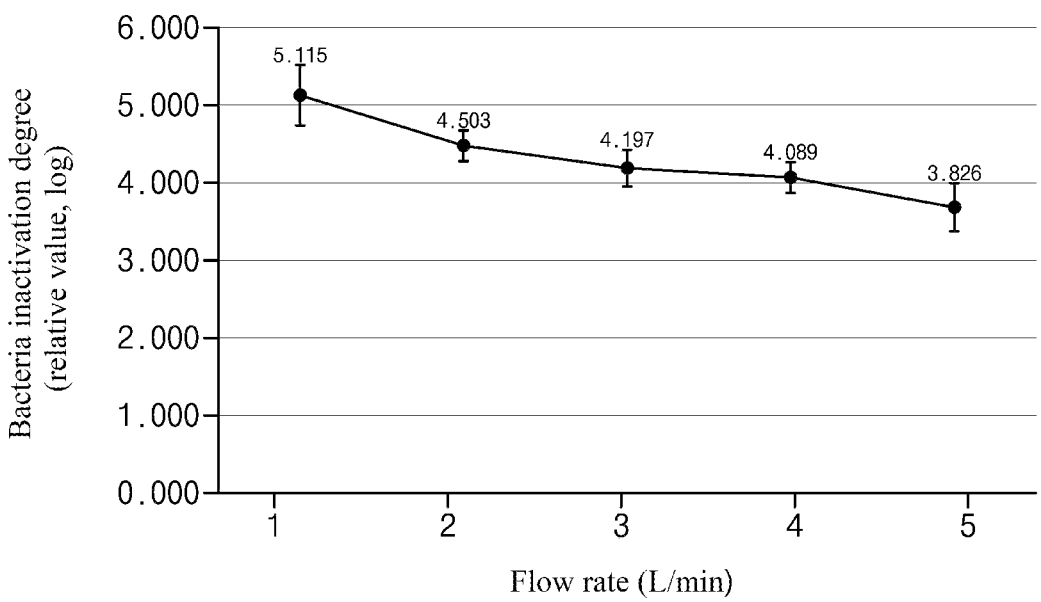
FIG. 12B is a graph depicting sterilization efficiency depending upon a different flow rate of the fluid flowing in the pipe of the fluid treatment module according to the embodiment of the present invention.

FIG. 11, FIG. 12A and FIG. 12B are graphs depicting sterilization efficiency depending upon the flow rate of the fluid flowing in the pipe of the fluid treatment module according to the embodiment of the present invention. FIG. 11 is a graph depicting the fluid treatment effect (sterilization effect) of the fluid treatment module shown in FIG. 9D, and FIG. 12A and FIG. 12B are graphs depicting the fluid treatment effect measured twice in use of the fluid treatment module shown in FIG. 9C.

Referring to FIG. 11, FIG. 12A, and FIG. 12B, the fluid treatment module according to the embodiment exhibited very gentle decrease in overall sterilization power, despite increase in flow rate of the fluid flowing in the pipe. In other words, as shown in FIG. 11, FIG. 12A and FIG. 12B, although the sterilization efficiency was gradually decreased as the fluid treatment speed was increased from 1 LPM to 5 LPM, the fluid treatment module exhibited a sterilization efficiency of 3 (log CFU/mL) or more due to insignificant reduction in sterilization power, despite increase in flow rate to five times of the initial flow rate. Accordingly, it can be seen that the fluid treatment module according to the embodiment can maintain high sterilization power despite increase in the fluid treatment speed, thereby increasing the volume of the fluid that can be sterilized thereby. In addition, the fluid treatment module according to the embodiment may be applied to a broad range of apparatuses by sufficiently ensuring sterilization power at various speeds. The fluid treatment module may be applied to various apparatuses, such as a water purifier, a washing machine, and a bidet, which may require different flow rates. As such, the fluid treatment module according to the embodiment may be applied to apparatuses requiring different flow rates.

Figure 13:
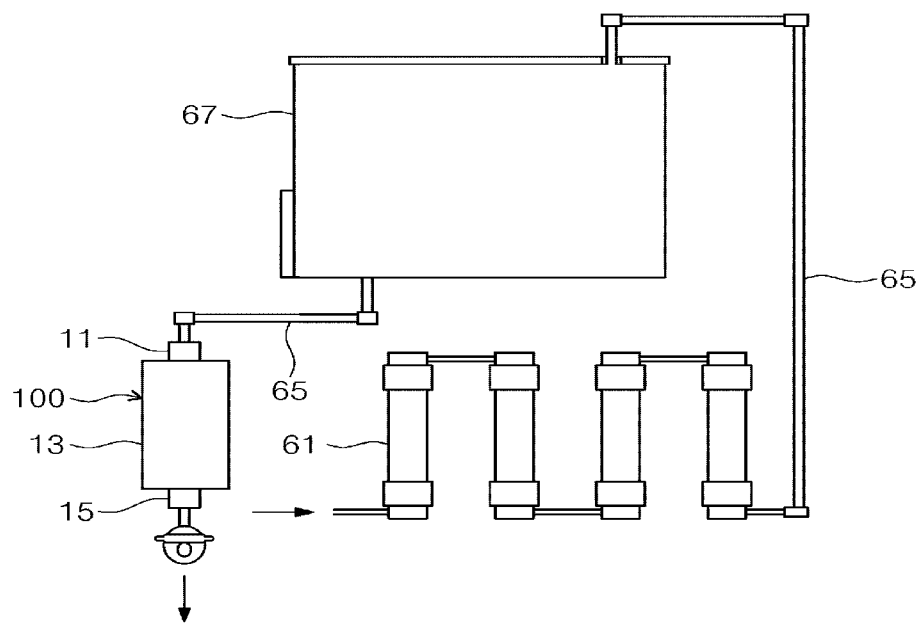
FIG. 13 is a schematic view of a water purifier adopting the fluid treatment module according to the embodiment of the present invention.

FIG. 13 is a schematic view of an apparatus, for example, a water treatment apparatus, adopting the fluid treatment module according to the fluid treatment module according to the embodiment of the present invention.

Referring to FIG. 13, the water treatment apparatus according to the embodiment includes filters 61 primarily filtering water, a reservoir 67 storing water having passed through the filters 61, and the fluid treatment module 100 connected to the reservoir 67.

The filters 61 serve to remove foreign matter from the supplied water. The water treatment apparatus may further include a pump (not shown) connected to the filters 61 to supply water to the filters 61. The filters 61 may be provided in various numbers, including filters for removing large impurities, filters for removing heavy metals and bacteria, and the like. In the case of sterilizing sufficiently purified water using the sterilizing device 100, the filters 61 may be omitted.

Water from which foreign matter is removed by the filters 61 is delivered to the reservoir 67 through a connection tube 65. The water treatment apparatus may be provided with at least one reservoir 67 or multiple reservoirs 67. Here, in a structure where water to be purified is supplied to the water treatment apparatus, the reservoir 67 may be omitted.

The fluid treatment module 100 treats water supplied from the reservoir 67. Here, treatment in the fluid treatment module 100 may refer to various treatments, such as sterilization, purification, deodorization, and the like, as described above. As shown in the drawings, the fluid treatment module 100 may be further provided with a draw valve to allow a user to dispense water immediately.

As such, with the fluid treatment module according to the present invention, it is possible to implement an apparatus having a very simple structure and high efficiency in treatment of air or water.

Although some embodiments have been described herein, it should be understood that these embodiments are provided for illustration only and are not to be construed in any way as limiting the present invention, and that various modifications, changes, alterations, and equivalents can be made by those skilled in the art without departing from the spirit and scope of the invention. Therefore, the scope of the present invention is not limited to the detailed description herein and should be defined only by the accompanying claims and equivalents thereto. For example, the above embodiments may be combined in various ways without departing from the sprit and scope of the present invention.

In addition, although advantageous effects provided by a certain configuration are not clearly described in description of the embodiments, it should be noted that expectable effects of the corresponding configuration should be acknowledged.

What is claimed is:

1. A fluid treatment module comprising:
a pipe including a flow channel in which fluid flows, the pipe having an inlet and an outlet;
a light source module comprising a substrate and at least one light emitting diode disposed in a mounting region located on an upper surface of the substrate and configured to emit light into the pipe to treat the fluid;
a reflector disposed inside the pipe to reflect the light emitted from the light source module and having higher reflectivity with respect to the light than the pipe; and
a heat dissipation plate arranged to be adjacent to the light source module and structured to dissipate heat from the light source module, the heat dissipation plate having higher thermal conductivity than thermal conductivity of the substrate of the light source module;
wherein the reflector comprises a first reflector disposed on an inner wall of the pipe and a second reflector disposed, on the substrate and having a ring shape with an opening penetrating through a center of the ring shape and exposing the mounting region of the substrate, the opening of the second reflector has a width gradually increasing in a direction further away from the surface of the substrate.

2. The fluid treatment module according to claim 1, wherein the heat dissipation plate has a larger area than the substrate.

3. The fluid treatment module according to claim 2, wherein the heat dissipation plate includes a metal.

4. The fluid treatment module according to claim 3, wherein the pipe further comprises a body extending in a longitudinal direction thereof, and first and second ends disposed in the longitudinal direction of the body.

5. The fluid treatment module according to claim 4, wherein the heat dissipation plate has a larger diameter than the body.

6. The fluid treatment module according to claim 1, wherein the inlet, the outlet, or both are provided in plural such that a flow speed and a flow direction of the fluid flowing into the pipe are controlled.

7. The fluid treatment module according to claim 1, wherein the reflector includes a porous material.

8. The fluid treatment module according to claim 1, wherein the reflector has a reflectivity of 80% or more.

9. The fluid treatment module according to claim 1, wherein the inlet and the outlet are provided in different numbers.

10. The fluid treatment module according to claim 9, wherein the inlet is provided as a pair and the outlet is provided singularly.

11. The fluid treatment module according to claim 10, wherein the inlet and the outlet have a same diameter.

12. The fluid treatment module according to claim 11, wherein the inlet and the outlet have different diameters.

* * * * *